United States Patent
Ghebre-Sellassie et al.

(10) Patent No.: US 10,010,620 B2
(45) Date of Patent: *Jul. 3, 2018

(54) TAMPER-RESISTANT PHARMACEUTICAL DOSAGE FORMS AND PROCESS FOR MAKING SAME

(71) Applicant: ExxPharma Therapeutics LLC, Morris Plains, NJ (US)

(72) Inventors: Isaac Ghebre-Sellassie, Morris Plains, NJ (US); Hibreniguss Terefe, Piscataway, NJ (US)

(73) Assignee: ExxPharma Therapeutics LLC, Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/058,955

(22) Filed: Mar. 2, 2016

(65) Prior Publication Data

US 2016/0175454 A1   Jun. 23, 2016

Related U.S. Application Data

(63) Continuation of application No. PCT/US2014/053758, filed on Sep. 2, 2014.

(51) Int. Cl.
| | | |
|---|---|---|
| A61K 47/58 | (2017.01) |
| B01F 7/00 | (2006.01) |
| A61K 47/48 | (2006.01) |
| A61K 31/138 | (2006.01) |
| A61K 31/485 | (2006.01) |
| A61K 9/20 | (2006.01) |

(52) U.S. Cl.
CPC ...... *A61K 47/48184* (2013.01); *A61K 9/2009* (2013.01); *A61K 9/2054* (2013.01); *A61K 9/2077* (2013.01); *A61K 31/138* (2013.01); *A61K 31/485* (2013.01); *A61K 47/58* (2017.08); *A61K 47/585* (2017.08); *B01F 7/00* (2013.01)

(58) Field of Classification Search
CPC .. A61K 9/2095; A61K 9/2077; A61K 9/2081; A61K 9/2086
See application file for complete search history.

(56) References Cited

U.S. PATENT DOCUMENTS

| | | |
|---|---|---|
| 7,157,103 B2 | 1/2007 | Sackler |
| 7,332,182 B2 | 2/2008 | Sackler |
| 7,399,488 B2 | 7/2008 | Hirsch et al. |
| 7,510,726 B2 | 3/2009 | Kumar et al. |
| 7,511,054 B2 | 3/2009 | Stinchcomb et al. |
| 7,658,939 B2 | 2/2010 | Oshlack et al. |
| 7,682,632 B2 | 3/2010 | Oshlack et al. |
| 7,718,192 B2 | 5/2010 | Oshlack et al. |
| 7,727,557 B2 | 6/2010 | Sackler |
| 7,771,707 B2 | 8/2010 | Hirsh et al. |
| 7,776,314 B2 | 8/2010 | Bartholmaus et al. |
| 7,790,215 B2 | 9/2010 | Sackler et al. |
| 7,842,307 B2 | 11/2010 | Oshlack et al. |
| 7,842,309 B2 | 11/2010 | Oshlack et al. |
| 7,842,311 B2 | 11/2010 | Oshlack et al. |
| 7,955,619 B2 | 6/2011 | Shah et al. |
| 8,017,148 B2 | 9/2011 | Sackler |
| 8,075,872 B2 | 12/2011 | Arkenau-Maric et al. |
| 8,097,278 B2 | 1/2012 | Sackler |
| 8,101,630 B2 | 1/2012 | Kumar et al. |
| 8,124,126 B2 | 2/2012 | Bosse et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,158,156 B2 | 4/2012 | Matthews et al. |
| 8,168,217 B2 | 5/2012 | Yum et al. |
| 8,211,905 B1 | 7/2012 | King et al. |
| 8,236,351 B2 | 8/2012 | Oshlack et al. |
| 8,252,328 B2 | 8/2012 | Tzannis et al. |
| 8,252,329 B2 | 8/2012 | Tzannis et al. |
| 8,273,798 B2 | 9/2012 | Bausch et al. |
| 8,298,579 B2 | 10/2012 | Abreu |
| 8,309,568 B2 | 11/2012 | Stinchcomb et al. |
| 8,323,889 B2 | 12/2012 | Arkenau-Maric et al. |
| 8,329,720 B1 | 12/2012 | King et al. |
| 8,337,888 B2 | 12/2012 | Wright et al. |
| 8,338,444 B1 | 12/2012 | King et al. |
| 8,349,362 B2 | 1/2013 | Soscia et al. |
| 8,354,124 B2 | 1/2013 | Yum et al. |
| 8,357,399 B2 | 1/2013 | Oschlack et al. |
| 8,362,029 B2 | 1/2013 | Evenstad et al. |
| 8,367,693 B1 | 2/2013 | King et al. |
| 8,372,432 B2 | 2/2013 | Han et al. |
| 8,377,453 B2 | 2/2013 | Han et al. |
| 8,383,152 B2 | 2/2013 | Jans et al. |
| 8,389,007 B2 | 3/2013 | Wright et al. |
| 8,394,408 B2 | 3/2013 | Han et al. |
| 8,409,616 B2 | 4/2013 | Kumar et al. |
| 8,415,401 B2 | 4/2013 | Yum et al. |
| 8,420,056 B2 | 4/2013 | Arkenau-Maric et al. |

(Continued)

FOREIGN PATENT DOCUMENTS

| | | |
|---|---|---|
| EP | 0367746 A2 | 5/1990 |
| EP | 0294103 B1 | 1/1995 |

(Continued)

OTHER PUBLICATIONS

Communication from U.S. Patent & Trademark Office, Office Action dated Sep. 18, 2015 for co-pending U.S. Appl. No. 14/157,658.

*Primary Examiner* — Gina Chieun Yu Justice
(74) *Attorney, Agent, or Firm* — Harvest IP Law LLP

(57) ABSTRACT

A process for the preparation of an erodible tamper-resistant dosage form that comprises a therapeutic agent-substrate complex embedded in a thermo-formable matrix, such that the complex includes at least one therapeutic agent bound to at least one substrate to form the therapeutic agent-substrate complex. The at least one substrate is being selected from a polyelectrolyte, an organic counter-ion, a pharmacologically inert organic component of a prodrug, an inclusion compound and an inorganic adsorbent; and the thermo-formable matrix includes one or more thermoplastic polymers and optionally at least one pharmaceutical additive. The dosage form provides resistance to intentional or unintentional tampering such as chewing, crushing and grinding, and volatilization.

5 Claims, 8 Drawing Sheets

(56) References Cited

U.S. PATENT DOCUMENTS

| | | |
|---|---|---|
| 8,420,120 B2 | 4/2013 | Yum et al. |
| 8,420,700 B1 | 4/2013 | Bausch et al. |
| 8,425,933 B2 | 4/2013 | Mehta |
| 8,445,018 B2 | 5/2013 | Habib et al. |
| 8,449,909 B2 | 5/2013 | Hirsh et al. |
| 8,460,640 B2 | 6/2013 | Vinson et al. |
| 8,461,137 B2 | 6/2013 | Mickle et al. |
| 8,465,774 B2 | 6/2013 | Breder et al. |
| 8,470,361 B2 | 6/2013 | Pettersson |
| 8,476,291 B1 | 7/2013 | King et al. |
| 8,481,560 B2 | 7/2013 | Stinchcomb et al. |
| 8,486,448 B2 | 7/2013 | Rahmouni et al. |
| 8,486,449 B2 | 7/2013 | Rahmouni et al. |
| 8,491,935 B2 | 7/2013 | Mehta et al. |
| 8,501,160 B2 | 8/2013 | Cailly-Dufestel et al. |
| 8,512,759 B1 | 8/2013 | McMahen et al. |
| 8,518,443 B2 | 8/2013 | Breder et al. |
| 8,524,275 B2 | 9/2013 | Oshlack et al. |
| 8,529,948 B1 | 9/2013 | Wright et al. |
| 8,557,291 B2 | 10/2013 | Rariy et al. |
| 8,563,038 B2 | 10/2013 | Andersen et al. |
| 8,569,329 B1 | 10/2013 | King et al. |
| 8,569,330 B1 | 10/2013 | King et al. |
| 8,575,151 B1 | 11/2013 | Bristol et al. |
| 8,586,088 B2 | 11/2013 | Oshlack et al. |
| 8,586,575 B1 | 11/2013 | King et al. |
| 8,597,684 B2 | 12/2013 | Mehta et al. |
| 8,603,526 B2 | 12/2013 | Tygesen et al. |
| 8,623,412 B2 | 1/2014 | Farid et al. |
| 8,623,418 B2 | 1/2014 | Liang et al. |
| 2005/0175733 A1 | 8/2005 | Thorengaard et al. |
| 2008/0075770 A1 | 3/2008 | Vaughn et al. |
| 2011/0020451 A1 | 1/2011 | Bartholomaus et al. |
| 2012/0148672 A1 | 6/2012 | Mehta et al. |
| 2013/0005823 A1 | 1/2013 | Emigh et al. |
| 2013/0022646 A1 | 1/2013 | Rudnic et al. |
| 2013/0045960 A1 | 2/2013 | Hirsh et al. |
| 2013/0122087 A1 | 5/2013 | Habib et al. |
| 2013/0122101 A1 | 5/2013 | Habib et al. |
| 2013/0129825 A1 | 5/2013 | Billoet |
| 2013/0171257 A1 | 7/2013 | Kumar et al. |
| 2013/0217716 A1 | 8/2013 | Wright et al. |
| 2013/0280176 A1 | 10/2013 | Diezi et al. |
| 2013/0280177 A1 | 10/2013 | Raman et al. |
| 2013/0281480 A1 | 10/2013 | Yum et al. |
| 2013/0287845 A1 | 10/2013 | Yum et al. |
| 2013/0289062 A1 | 10/2013 | Kumar et al. |
| 2013/0295168 A1 | 11/2013 | Yum et al. |
| 2013/0295170 A1 | 11/2013 | Dordunoo |
| 2013/0310413 A1 | 11/2013 | Hirsh et al. |
| 2013/0337059 A1 | 12/2013 | Yum et al. |
| 2013/0337060 A1 | 12/2013 | Yum et al. |
| 2013/0338229 A1 | 12/2013 | King et al. |
| 2013/0344143 A1 | 12/2013 | Rosenberg et al. |
| 2014/0004191 A1 | 1/2014 | Rahmouni et al. |
| 2014/0010860 A1 | 1/2014 | Odidi et al. |
| 2014/0010873 A1 | 1/2014 | Tygesen et al. |
| 2014/0010874 A1 | 1/2014 | Sackler |
| 2014/0010875 A1 | 1/2014 | Huang |
| 2014/0011832 A1 | 1/2014 | Huang |
| 2014/0011842 A1 | 1/2014 | Scicinski et al. |
| 2014/0017310 A1 | 1/2014 | Gower et al. |
| 2014/0271857 A1* | 9/2014 | Nelson ............... A61K 31/245 424/475 |

FOREIGN PATENT DOCUMENTS

| | | |
|---|---|---|
| EP | 0565301 B1 | 2/1999 |
| WO | 1992011871 A1 | 7/1992 |
| WO | 1998027961 A2 | 7/1998 |
| WO | 2006106344 A2 | 10/2006 |
| WO | 2012061779 A1 | 5/2012 |
| WO | 2012112952 A1 | 8/2012 |
| WO | 2013077851 A1 | 5/2013 |
| WO | 2013128276 A2 | 9/2013 |
| WO | 2013153451 A2 | 10/2013 |
| WO | 2013158810 A1 | 10/2013 |
| WO | 2013158814 A1 | 10/2013 |
| WO | 2014006004 A1 | 1/2014 |
| WO | 2014011830 A1 | 1/2014 |

* cited by examiner

| Assay (% Labeled Claim) Accelerated Stability 40°C/75%RH | | | | |
|---|---|---|---|---|
| Formulation ID | $T_0$ | 1Mo | 2 Mo | 3 Mo |
| F23 | 97.9 | 97.9 | 98.4 | 100.2 |
| F41 | 99.5 | 98.3 | 99.3 | 98.6 |
| F46 | 100.7 | 102.2 | 98.6 | 98.8 |
| F64 | 99.3 | 103.4 | 100.7 | 100.3 |

TAMPER-RESISTANT PHARMACEUTICAL DOSAGE FORMS AND PROCESS FOR MAKING SAME

CROSS REFERENCE TO RELATED APPLICATIONS

This application is a continuation application filed under 35 U.S.C. § 111(a), claiming the benefit under 35 U.S.C. § 120 and § 365(c) of a PCT International Application PCT/US2014/053758, filed on Sep. 2, 2014, which in turn is based on, and claims the benefit of U.S. Provisional Patent Application No. 61/959,830, filed Sep. 3, 2013, and U.S. patent application Ser. No. 14/157,658, filed Jan. 17, 2014, and U.S. patent application Ser. No. 14/323,412, filed Jul. 3, 2014, which are incorporated herein by reference in their entirety.

FIELD OF THE INVENTION

The present invention relates to an improved pharmaceutical dosage form. More particularly, the invention relates to a tamper-resistant dosage form that comprises a therapeutic agent-substrate complex and a thermo-formable matrix and to a method of making same.

BACKGROUND OF INVENTION

Product tampering occurs when a dosage form is manipulated to achieve an objective in ways that is not intended per dosing instructions. It may involve drug abusers who tamper with the dosage form to obtain euphoria, or non-abusers such as patients and caregivers who innocently tamper with the dosage form to address legitimate concerns. For example, an elderly patient may break a dosage form to facilitate swallowing or a caregiver may break a dosage form to reduce the therapeutic dose.

Prescription medications are being abused at an alarming rate. The most commonly abused classes of prescription drug products are opioids (narcotics), sedatives/hypnotics, stimulants, and tranquilizers. The most commonly abused over-the-counter drugs are decongestants, antihistamines and cough medicines. An estimated 52 million people have used prescription drugs for nonmedical reasons at least once in their lifetimes.

Particularly, abuse of prescription painkillers is a growing, public health problem that has been steadily worsening as reflected in increased treatment admissions, emergency room visits, and overdose deaths. About 164 million patients/year visit the doctor office for pain of which 20% receive opiate prescriptions for pain treatment. Number of opiate prescriptions has been steadily increasing since 1991. In 2013 alone, 230 million opioid prescriptions were dispensed. The pain management market generated $7.3 billion in US sales in 2012. The market is predicted to increase to $9.8 billion by 2018 and to $11.3 billion by 2023.

In 2010, more than 40% of all drug poisoning deaths involved opioid analgesics, and the number of overdose deaths involving opioid analgesics has more than tripled since 1999. The CDC's latest figures show that 16,500 people died from overdoses tied to common narcotic pain relievers in 2010. Over dosage of opiates occurs due to intentional or unintentional tampering of opiate drug products. Abusers tamper with dosage form to obtain euphoria, while patients/caregivers manipulate dosage forms to facilitate dosing. Pain relievers, such as OxyContin® and Vicodin®; anti-depressants, such as Xanax® and Valium®, and stimulants, such as Concerta®, Adderall®, are the most commonly abused prescription drugs.

While drug abuse has been common with all dosage forms, modified release products have been particularly attractive to drug abusers due to the high drug content in the dosage forms. When these dosage forms are tampered with or altered, they may lead to more rapid release of the therapeutic agent, which in turn may provide the drug abusers with greater euphoria that they desperately desire.

To address the drug abuse epidemic, pharmaceutical companies have started to develop abuse deterrent formulations and the U.S. Food and Drug Administration (FDA) has also issued a guideline to encourage development of more effective tamper-resistant formulations. Abuse deterrent formulations are designed to thwart deliberate attempts by drug-abusers to extract the active ingredient or blunt the euphoric effects from unapproved methods of administration.

Common methods of drug abuse include: (1) oral ingestion, where the dosage form is chewed, to destroy the release controlling matrix and deliver high doses of therapeutic agent into the gastrointestinal tract, and swallowed, with or without co-ingestion of alcohol; (2) intravenous injection, which involves extraction of the therapeutic agent from the dosage form using an appropriate solvent, followed by injection of the therapeutic agent directly into the blood stream; (3) nasal snorting, where the dosage form is crushed, milled, or ground into a fine powder and administered intra-nasally to facilitate rapid drug absorption through the lining of the nasal passages; and (4) smoking, where the therapeutic agent is vaporized for inhalation by subjecting the dosage form to heat.

In addition, dosage forms, particularly modified release dosage forms, are relatively large in size and may pose a dosing challenge to many people including the elderly and young. Often, patients and caregivers may break the dosage form to reduce the size. By doing so, they inadvertently compromise the release controlling mechanism of the dosage form and potentially lead to dose dumping, often with adverse consequences.

To circumvent dosage form tampering, many tamper resistant formulations have been described.

U.S. Pat. No. 7,510,726 describes a therapeutic pharmaceutical composition comprising a mixture consisting of at least one opioid analgesic, gel forming polyethylene oxide, and at least one disintegrant. Due to the physical properties of the gel forming polymer, the extended release properties of the disclosed dosage form is expected to be compromised upon mastication and not prevent abuse by chewing and swallowing.

U.S. Pat. No. 7,771,707 describes a solid abuse deterrent pharmaceutical composition of a pharmaceutically active agent prone to abuse, and one or more fatty acids or fatty amines present in molar excess relative to the pharmaceutically active agent. As taught, the fatty acids and fatty acid amines which impart lipophilicity on the drug substance may be susceptible to physical instability.

U.S. Pat. No. 7,776,314 describes parenteral abuse-proofed solid dosage form for oral administration, comprising one or more active ingredients with potential for abuse, and at least one viscosity-increasing agent. Invention deters only abuse by injection.

U.S. Pat. No. 8,075,872 describes an abuse resistant dosage form thermoformed by extrusion and having a breaking strength of at least 500 N, which contains a mixture of one or more active ingredients with abuse potential, polyalkylene oxides, physiologically acceptable auxiliary substances, and optionally wax and cellulosic derivatives. The disclosed dosage form contains low $t_g$ hydrophilic polymers that may not withstand mastication when exposed to saliva due to plasticization.

U.S. Pat. No. 8,409,616 describes a therapeutic pharmaceutical composition comprising a water-soluble drug susceptible to abuse, a gel forming polymer and a disintegrant. As taught, the gel forming polymers based on polyethylene oxide are susceptible to chewing and mastication upon contact with saliva.

U.S. Pat. No. 8,449,909 describes a therapeutically effective pharmaceutical composition comprising solid microparticles, wherein the microparticles comprise an active agent, one or more fatty acids, and one or more carrier materials selected from waxes or wax-like substances. The fatty acids and fatty acid amines, as taught, impart lipophilicity on the drug substance but may not ensure physical stability upon storage. U.S. Patent Application Publication 2008/0075770 describes a monolithic solidified oral dosage form prepared by a thermal process comprising a therapeutic agent and a hydrophilic polymer. The disclosed drug molecules incorporated in a hydrophilic polymeric matrix have a tendency to diffuse when mobility of the polymer is increased due to solvent or temperature effect, thereby increasing extractability.

U.S. Pat. No. 8,486,448 describes a controlled release formulation comprising a core comprising a superabsorbent material, a controlled release coat surrounding the core; and a plurality of controlled release microparticles containing a pharmaceutically active agent. This abuse deterrent relies on a hard coating that may be susceptible to extraction by both aqueous and organic solvents.

U.S. Pat. No. 8,202,542 describes an abuse resistant opioid drug-ion exchange resin complexes having hybrid coatings containing a cured polyvinylacetate polymer and a pH-dependent enteric coating layer mixed therein. As taught, these polymer coatings are soluble in aqueous or organic solvents which would make the dosage form susceptible abuse by extraction.

U.S. Patent Application Publication 2011/0020451 describes a tamper-resistant thermoformed pharmaceutical dosage form having a breaking strength of at least 300 N and comprising an opioid, a physiologically acceptable acid and a polyalkylene oxide. The disclosed dosage form is expected to be susceptible to abuse by chewing and swallowing.

U.S. Patent Application Publication 2012/0148672 describes a coated modified release opioid-ion exchange resin complex comprising a pharmaceutically effective amount of an opioid bound to a pharmaceutically acceptable ion exchange resin complex; and a pH-independent, high tensile strength, water permeable, water insoluble, diffusion barrier coating. As disclosed, the coating is expected to dissolve in organic solvents and high aqueous pH, which would make the dosage form reduce extraction by the complexing ion exchange resin only.

As a result, in spite of the various tamper-resistant formulation approaches mentioned above, there is still a need for improved abuse deterrent formulations that better prevent common methods of dosage form tampering and associated drug abuse administration routes with or without the incorporation of aversive agents and agonist/antagonists in the dosage form.

In particular, the present invention eliminates or reduces all forms of tampering, and hence all modes of abuse. The invention relates to an erodible dosage form that has a dry core which hydrates on the surface upon exposure to extraction fluid to form a thin gel layer that limits water penetration into the core. The dosage form also has a synchronized barrier system that provides it with plasticity and hardness that renders the dosage form resistant to chewing, crashing and grainding, and volatilization.

SUMMARY OF THE INVENTION

According to one embodiment, the present invention is related to an erodible tamper-resistant dosage form that includes at least one therapeutic agent, at least one substrate, at least one thermoplastic polymer, and optionally at least one pharmaceutical additive, such that the at least one therapeutic agent and the at least one substrate form a therapeutic agent-substrate complex, the at least one thermoplastic polymer and the optionally at least one pharmaceutical additive form a thermo-formable matrix, and the therapeutic agent-substrate complex is embedded in the thermo-formable matrix. The ratio of the at least one therapeutic agent to the at least one substrate is from 1:20 to 20:1 by weight, and the ratio of the therapeutic agent-substrate complex to the thermo-formable matrix is from 1:20 to 20:1 by weight. Optionally, a free therapeutic agent or a substrate is embedded in the erodible thermo-formable matrix along with the therapeutic agent-substrate complex.

According to another embodiment, the present invention is related to a process of preparing an erodible tamper-resistant dosage form, including the steps of: (1) blending at least one therapeutic agent and at least one substrate in a therapeutic agent-to-substrate ratio from 1:20 to 20:1 by weight; (2) reacting the at least one therapeutic agent and the at least one substrate to form a therapeutic agent-substrate complex; (3) forming a thermo-formable matrix blend with at least one thermoplastic polymer and optionally at least one pharmaceutical additive; (4) mixing the therapeutic agent-substrate complex and the thermo-formable matrix blend in a ratio from 1:20 to 20:1 by weight; (5) granulating the therapeutic agent-substrate complex and the thermo-formable matrix blend to form the tamper-resistant dosage form in which the therapeutic agent-substrate complex is embedded in the thermo-formable matrix; and (6) shaping the tamper-resistant dosage form into one of an immediate release or modified release tablet form and an immediate release or modified release multiparticulate form, and optionally film-coating the tablets and multiparticulates.

BRIEF DESCRIPTION OF THE DRAWINGS

FIG. 6 shows the 3-month accelerated chemical stability.

DETAILED DESCRIPTION OF THE INVENTION

Figure 1:
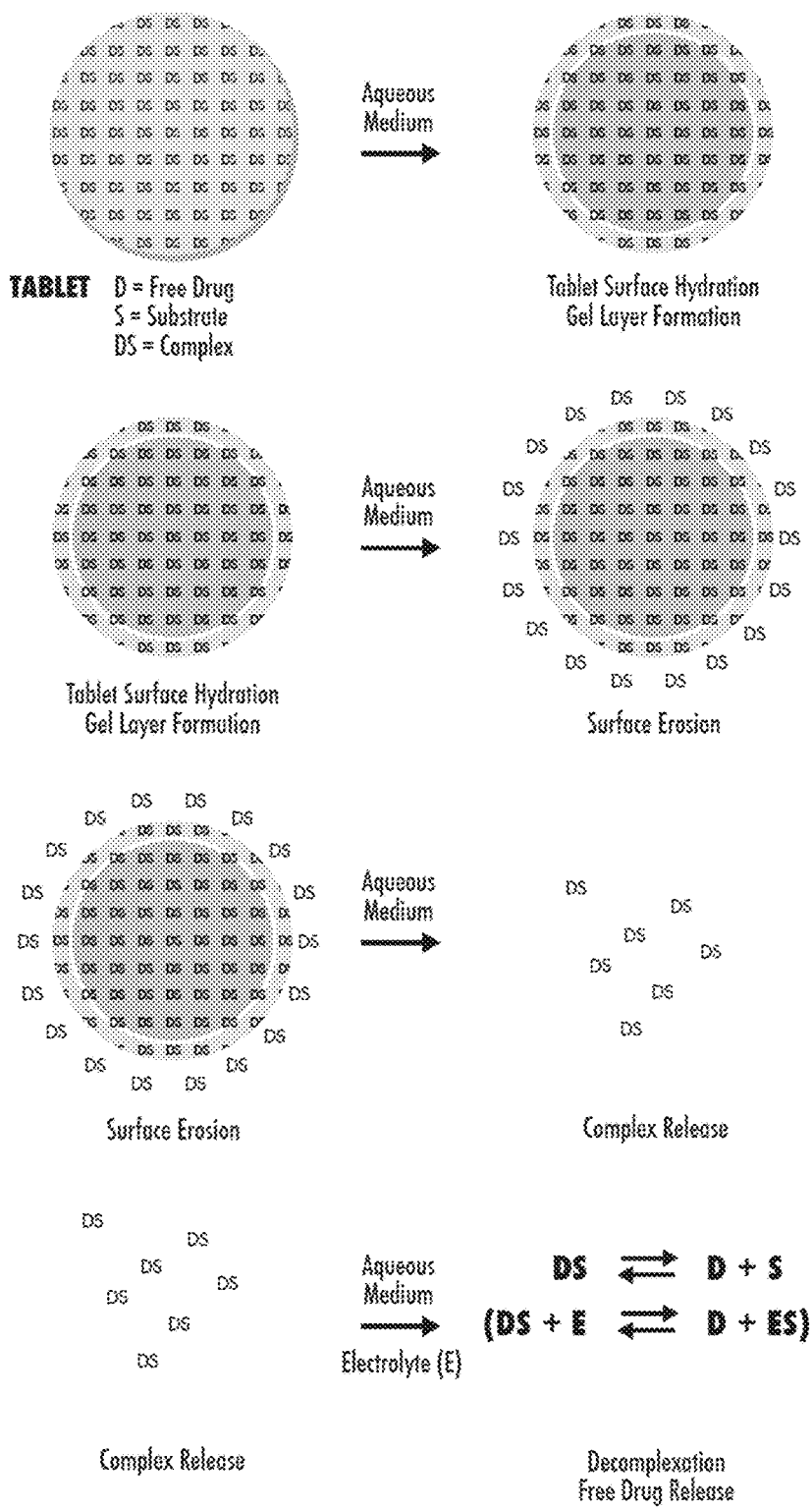
FIG. 1 shows a schematic drawing describing the drug release mechanism of the erodible tamper-resistant dosage forms.

One part of the invention is related to an erodible tamper-resistant dosage form that is resistant to various tampering modes. Another part of the invention is related to a process of making the erodible tamper-resistant dosage form.

Definitions

According to the disclosure, a "therapeutic agent" means a substance that elicits a pharmacologic response when administered by a patient or drug abuser. "Therapeutic agent" and "drug" are terms that are used interchangeably. "Substrate" means a substance that interacts with the therapeutic agent to form a complex. "Complex" means a chemical association of a drug substance with a substrate through ionic bonds, polar covalent bonds, covalent bonds, and hydrogen bonds. A "prodrug" is substance that converts into an active form through enzymatic cleavage when ingested, and considered a complex according to the disclosure. A "pharmaceutical additive" is a substance that is added to formulations to improve functionality and processability of the dosage forms. A "thermoplastic" polymer is a polymer that is solid at room temperature, and becomes pliable and moldable at elevated temperatures. "Tampering" means an intentional or an unintentional manipulation of dosage forms in a manner that is not intended for by dosing instructions, such as by chewing, crushing, grinding, extraction and volatilization. "Monolithic tablets" means single tablet dosage forms comprising of homogeneous solid matrix or structure greater than 5 mm in size. "Multiparticulates" means homogeneous micro-particles or mini-tablets that are less than 5 mm in diameter and could be filled in capsules or compressed into tablets. Synchronized barrier system" means is a barrier where independent barriers are synergically combined to form an enhanced barrier system. "Release mechanism" means the kinetics of drug release from a dosage form. "Drug-independent template formulation" means a formulation that provides similar tamper-resistance and drug release profiles when one drug substance is replaced with another drug substance in a given formulation. "Physical stability" means the microstructure of internal and external structure of a dosage form is not altered upon storage. "Chemical stability" means the integrity of a chemical constituent in a dosage form is not altered upon exposure to environmental factors. "Release profile" means a pattern of release of a drug from a dosage form in a dissolution medium as a function of time. "Erodible" means a solid matrix that hydrates in a dissolution medium and dissolves from the surface. "Erodible tamper-resistant dosage form" means the dosage form hydrates and dissolves from the surface at a controlled rate without being affected by common tools of tampering methods. "Erodible thermo-formable matrix" means a solid structure composed of thermally moldable formulation components that hydrates and dissolves from the surface at a controlled rate without being affected by common tools of tampering methods. "Reactive extrusion process" means a continuous twin screw-based mixing process where oppositely charged molecules and particles are intimately mixed to bring about a close association of the two entities. "Particle size" means a dimensional measurement of a particle. "Granulation process" means a process of forming granules through blending and intimate mixing of drug substances and pharmaceutical additives and an input of energy. "Melt granulation" means a process of forming granules from a blend of drug substances and pharmaceutical additives with the help of heat energy. "Wet granulation" means a process of forming granules from a blend of drug substances and pharmaceutical additives with the help of water or solvents. "Dry granulation" means a process of forming granules from a blend of drug substances and pharmaceutical additives with the help of pressure.

Erodible Tamper-Resistant Dosage Form

The erodible tamper-resistant dosage form comprises a therapeutic agent-substrate complex embedded in a thermo-formable matrix. Specifically, the erodible tamper-resistant dosage form includes at least one drug, at least one substrate, at least one thermoplastic polymer and optionally at least one pharmaceutical additive that are arranged in the following manner: the at least one drug and the at least one substrate form a drug-substrate complex, the at least one thermoplastic polymer and optionally the at least one pharmaceutical additive form a thermo-formable matrix, and the drug-substrate complex is dispersed and embedded in the thermo-formable matrix.

It has been discovered that a therapeutic agent-substrate complex embedded into a thermo-formable matrix is effective against all forms of product tampering and drug abuse without the use of aversion agents and antagonists. A complex of the therapeutic agent and a substrate is formed first prior to the incorporation into the thermo-formable matrix in order for the formulation to provide tamper-resistance. While pre-formation of the complex is preferred for optimal performance, in some cases, particularly with inorganic additives, the drug-substrate association could occur in situ during processing. Alternatively, a prodrug, which is comprised of a covalently bonded drug with an organic moiety, is embedded in the erodible thermo-formable matrix in place of the therapeutic agent-substrate complex.

The therapeutic agent-substrate complex and the thermo-formable matrix should interact as described above in order to achieve resistance to tampering. In contrast, the formulations in Examples 2, 3 and 4 do not achieve resistance to tampering: (1) if only the therapeutic agent-substrate complex is used without the thermo-formable matrix (see Example 2); (2) if the therapeutic agent is dispersed in the thermo-formable matrix without a substrate (see Example 3); and (3) if only a blend of the therapeutic agent and the substrate but not a complex is dispersed in the thermo-formable matrix (see Example 4).

The tamper-resistant dosage form could be tablets or multi-particulates with the same or similar composition, the only difference being size which results from differences in downstream processing. The tablets are formed through compression while the multi-particulates are prepared through pelletization.

Therapeutic Agents

Therapeutic agents covered by the present invention include those that are susceptible to abuse, i.e. "abuse-prone", and those that are not susceptible to abuse, i.e. "not abuse-prone".

In one aspect, abuse-prone therapeutic agents comprise, but not limited to, alfenatil, allylprodine, alphaprodine, anileridine, apomorphine, apocodeine, benzylmorphine, benzitramide, buprenorphine, butorphanol, clonitrazene, codeine, codeine methylbromide, codeine phosphate, codeine sulfate, cyclazocine, cyclorphen, cyprenorphine, desmorphine, dextromethorphan, dextromoramide, dezocine, diamromide, dihydrocodeine, dihydrocodeinone, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, hydrocodone, hydrocodone barbiturate, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, morphine, morphine derivatives, myrophine, nalbuphine, narceine, nicomorphine, norlevorphanol, normethadone, nalorphine, normorphine, norpipanol, ohmefentanyl, opium, oxycodone, oxymorphone, papaverum, pentazocine, phenadoxone, phenomorphan, phenazocine, phenoperidine, pheoperidine, pholcodine, piminodine, piritramide, propheptazine, promedol, profadol, properidine, propiram, propoxyphene, remifentanyl, sufentanyl, tramadol, tilidine, naltrexone, naloxone, nalmefene, methylnaltrexone, naloxone methiodide, naloxonazine, trindole, naltrindole isothiocyanate, naltriben, norbinaltorphimine, funaltrexmine, and salts or esters of any of the opioids, acecabromal, bomisovalum, capruide, cabromal, ectylurea, chlorhexadol, ethcholorvynol, meparfynol, 4-methyl-5-thiazolethanol, tetrapentylalcohol, butoctamide, diethylbromoacetamide, ibrotamide, isovarleryl diethylamide, niaprazine, triacetamide, trimetozine, zolpidem, zopiclone; barbituric acid derivatives such as allobarbital, amobarbital, aprobarbital, barbital, brallabarbital, butabarbital sodium, butabarbital, butallylonal, buthetal, carbubarb, cyclobarbital, cyclopentobarbital, enallylpropymal, 5-ethyl-5-(1-piperidyl) barbituric acid, 5-furfuryl-5-isopropylbarbituric acid, heptabarbital, hexethal sodium, hexobarbital, mephobarbital, methitural, narcobarbital, nealbarbital, pentobarbital sodium, phenallylmal, phenobarbital, phenobarbital sodium, phenylmethylbarbituric acid, probarbital, propallylonal, proxibarbal, reposal, secobarbital sodium, thiopental, talbutal, tetrabarbital, thiobarbital, thiamylal, vinbarbital sodium, and vinylbital, benzodiazepine derivatives such as alprazolam, brotizolam, clorazepate, chlordiazepoxide, clonazepam, diazepam, doxefazepam, estazolam, flunitrazepam, flurazepam, haloxazolam, lorazepam, loprazolam, lormetazepam, nitrazepam, quazepam, temazepam, and triazolam; carbamates such as amylcarbamate, ethinamate, hexaprypymate, meparfynol carbamate, novonal and trichlorourethan; chloral derivatives such as carbocloral, chloral betaine, chloral formamide, chloral hydrate, chloralantipyrine, dichloralphenazone, pentaerithriol chloral and tricloflos; piperidinediones such as gluthemide, methylprylon, piperidione, taglutimide, thalidomide; quinazolone derivatives such as etaqualone, mecloquanone, and methaqualone; and others such as acetal, acetophenone, aldol, ammonium valerate, amphenidone, d-bornyl-a-bromoisovalerate, d-bornylisovalerate, calcium 2-ethylbutanoate, carfinate, a-chlorolose, clomethiazole, cypripedium, doxylamine, etodroxizine, etomidate, fenadiazole, homofenazine, hydrobromic acid, mecloxamine, methyl valerate, opium, paraldehyde, perlapine, propiomazine, rimazafone, sodium oxybate, sulfomethylmethane, sulfonmethane, amphethamine, dextroamphethamine, levoamphethamine, methamphethamine, methylphenidate, phenmetrazine, modatinil, avafinil, armodafinil, and ampalimes; cannabinoids such as tetrahydro-cannabinol, nabilone; ketamine, tiletamine, dextromethorphan, ibogaine, dixocilpine; anabolic steroids such as androisoxazole, androstenediol, bolandiiol, clostebol, ethylesternol, formyldienolone, 4-hydroxy-19-nortestosterone, methandriol, methenolone, methyltrienolone, nandrolone, nandrolone deconate, nandrolone p-hexyloxyphenylpropionate, nandrolone phenpropionate, norbolethone, oxymestrone, pizotyline, quinbolone, stenbolone and trenbolone; anorexics such as aminorex, amphecloral, benzaphetamine, chlorphentermine, clobenzorex, cloforex, clortermine, cyclexedrine, diethylpropion, diphemethoxidine, n-ethylamphetamine, fenbutrazate, fenfluramine, fenproporex, furfurylmethylamphetamine, levophacetoperate, mazindol, mefenorex, metamfeproamone, norpseudoephedrine, phendimetrazine, phendimetrazine trtrate, phentermine, phenylpropanolamine hydrochloride, picilorex, pseudoephedrine, ephedrine, levo-methamphetamine, phenylpropanolamine, propylhexedrine and synephrine.

In another aspect, therapeutic agents that are not susceptible to abuse comprise, but not limited to, atenolol, albendazole, alendronate, alprostadil, allopurinol, amlexanox, anagrelide, aminophylline, alitretinoin, amodiaquine, astemizole, atovaquone, aztreonam, atorvastatin, azlocillin, baclofen, benazepril, benzonatate, bitolterol mesylate, brompheniramine, cabergoline, carisoprodol, celecoxib, cefpiramide, chlorothiazide, chlormezanone, cimetidine, cetirizine, cefotaxime, ciprofloxacin, cephalexin, chloroquine, clomocycline, cyclobenzaprine, cyproheptadine, cyproheptadine, cefmenoxime, cyclophosphamide, ciclopirox, cladribine, chlorpheniramine, chlorzoxazone, clemastine, clofarabine, cytarabine, dacarbazine, dantrolene, daunorubicin, dexamethasone, diclofenac, diethylcarbamazine, diphenhydramine, diphenylpyraline, disopyramide, diltiazem, dopamine, dofetilide, doxazosin, enoxacin, epirubicin, eplerenone, erlotinib, ertapenem, etoposide, exemestane, ezetimibe, fexofenadine, flucloxacillin, fulvestrant, fenofibrate, fenoprofen, fenoldopam, fluocinonide, flunisolide, fluorouracil, gefitinib, gemcitabine, grepafloxacin, guaifenesin, halofantrine, ibuprofen, ibandronate, ipratropium, irinotecan, isosorbide mononitrate, ipratropium, ivermectin, ketoconazole, ketoprofen, ketorolac, levamisole, letrozole, levosimendan, levofloxacin, lovastatin, loratadine, lymecycline, loracarbef, lisuride, meclofenamate, mefloquine, meloxicam, methocarbamol, methylbromide, metolazone, methyldopa, methdilazine, mequitazine, mitotane, mivacurium, moxifloxacin, mometasone, midodrine, milrinone, nabumetone, naproxen, nifedipine, nilutamide, nedocromil, omeprazole, olmesartan, oxaliplatin, oxamniquine; orphenadrine, pantoprazole, pefloxacin, pentamidine, penicillamine, pemetrexed, perhexiline, phenylbutazone, pipobroman, piroxicam, propafenone, propranolol, phentermine, phentolamine, piperacillin, piperazine, primaquine, piroxicam, pivoxil, praziquantel, pregablin, probenecid, porfimer, propafenone, prednisolone, proguanil, pyrimethamine, quinine, quinidine, ranolazine, remikiren, rofecoxib, salmeterol, sulfanilamide, sulfadiazine, suprofen, sulfinpyrazone, tenoxicam, triamterene, tolmetin, toremifene, tolazoline, tamoxifen, teniposide, theophylline, terbutaline, terfenadine, thioguanine, tolmetin, trimetrexate, triprolidine, trovafloxacin, verapamil, valsartan, vinorelbine, valrubicin, vincristine, valdecoxib and mixtures thereof.

Substrates

The invention relates to a tamper-resistant dosage form comprising one or more substrates such as polyelectrolytes, organic counter ions, inorganic adsorbents, pharmacologically inert components of prodrugs, and inclusion compounds. According to the invention, a "substrate" is a substance that interacts with a therapeutic agent to form a complex. "Complex" means a chemical association between a therapeutic agent and a substrate through ionic bonds, covalent bonds, polar covalent bonds, and hydrogen bonds.

In one aspect, substrates comprise polyelectrolytes consisting of natural polyelectrolytes selected, for example, from the group consisting of nucleic acids, poly (L-lysine), poly (L-glutamic acid), carrageenan, alginates, and hyaluronic acid, and mixtures thereof; chemically modified polyelectrolyte selected, for example, from the group consisting of pectin, chitosan (deacetylation of chitin), cellulose-based, starch-based and dextran-based polymers and mixtures thereof; and synthetic polyelectrolytes selected from, for example, poly(vinylbenzyl trialkyl ammonium), poly(4-vinyl-N-alkyl-pyridimiun), poly(acryloyl-oxyalkyl-trialkyl ammonium), poly(acryamido-alkyl-trialkyl ammonium), poly(diallydimethyl-ammonium), poly(acrylic or methacrylic acid), and poly(itaconic acid) and maleic acid/diallyamine copolymer, crosslinked copolymers such as carbopols, crosscarmellose, ion exchange resins and mixtures thereof.

Examples of ion exchange resins include sulfonated copolymer of styrene and divinylbenzene, a carboxylate copolymer of styrene and divinylbenzene, a copolymer of styrene and divinylbenzene containing quaternary ammonium groups such as Amberlite® IR-120, Amberlite® XE-69, Amberlite® IRP-64/69, Dowex® 50WX2, Dowex® 50WX4, Dowex® 50WX8,f Duolite® AP 143, Indion® 204, Indion® 214, Indion® 234, Indion® 264, Tulsion® 335, Tulsion® 339, and Tulsion® 343 and mixtures thereof.

In yet another aspect, substrates comprise organic counter ions selected from the group, for example, consisting of but not limited to acetic acid, adipic acid, arachidonic acid, benzenesulfonic acid, capric acid, caprylic acid, citric acid, dihomoy-linoleic acid, docesenoic acid, docosatetraenoic acid, docosohexaconic acid, docosopentanoic acid, eicosapentanoic acid, fumaric acid, gondoic acid, lauric acid, linoleic acid, α-linoleic acid, 6-linoleic acid, maleic acid, myristic acid, nervonic acid, oleic acid, oleostearic acid, oxalic acid, palmitic acid, palmitoleic acid, stearic acid, succinic acid, tartaric acid, vaccenic acid, and mixtures thereof.

In another aspect, substrates comprise inorganic adsorbents selected, for example, from the group consisting of but not limited to aluminum silicate, attapulgite, bentonite, calcium silicate, kaolin, lithium magnesium aluminum silicate, lithium magnesium silicate, lithium magnesium sodium silicate, magnesium silicate, magnesium trisilicate, montmorillonite, pyrophyllite, sodium magnesium silicate, zeolite, and zirconium silicate and mixtures thereof.

In yet another aspect, substrates comprise pharmacologically-inert organic component of prodrugs is selected, for example, from the group consisting of but not limited to amides and esters.

In yet another aspect, substrates comprise inclusion compounds selected, for example, from the group consisting of but not limited to α-cyclodextrins, β-cyclodextrins and γ-cyclodextrins.

Thermoplastic Polymers

The invention relates to a tamper-resistant dosage form that comprises one or more thermoplastic polymers such as, but not limited to, cellulose derivatives, or non-cellulosic derivatives that include vinyl derivatives, acrylates, polyoxides, polysaccharides and polyglycols. A "thermoplastic" polymer is a polymer that is solid at room temperature, and becomes pliable and moldable at elevated temperatures. A critical property of thermoplastic polymers is the glass transition temperature, a temperature where the polymer changes or transitions from a solid glassy phase into a rubbery phase. Glass transition temperatures are lowered by incorporating plasticizers.

Examples of cellulose derivatives suitable for the present invention include, but not limited to, hydroxypropyl cellulose, hydroxylpropyl methylcellulose, methylcellulose, hydroxyl ethyl cellulose, and mixtures thereof.

Examples of non-cellulose derivatives suitable for the present invention include, but not limited to, methylmethacrylate, carrageenan, xanthan gum, polyethylene glycol, polyethylene oxide, polypropylene glycol, polyvinyl acetate, polyvinyl alcohol, polyvinyl pyrrolidone, butyl/methylmethacrylate-dimethylaminoethylmethacrylate copolymer, and polyvinyl caprolactam-polyvinyl acetate-polyethylene glycol, and mixtures thereof.

Pharmaceutical Additives

The invention relates to a dosage form optionally comprising pharmaceutical additives that improve functionality and processability of dosage forms. Pharmaceutical additives that are incorporated in formulations include plasticizers, waxes, surfactants, inorganic fillers, anti-adherents, erosion enhancers, anti-oxidants, and buffering agents.

Examples of plasticizers include, but not limited to, dibutyl sebacate, glycerol, polyethylene glycol, propylene glycol, triacetin, tributyl citrate, and triethyl citrate and mixtures thereof.

Examples of waxes include, but not limited to, bees wax, candilila wax, carnuba wax, and paraffin wax and mixtures thereof.

Examples of surfactants include, but not limited to, alkyl benzene sulfones, alkyl sulfates, ether carboxylates, glycerol/propylene glycol fatty acid esters, hexadecyl triammonium bromide, hydroxylated lecithin, lauryl carnitine, lower alcohol-fatty acid esters, mono-/di-glycerides, Ovothin®, polyethylene glycol alkyl ethers, polyethylene glycol-fatty acid monoesters, polyethylene glycol-fatty acid diesters, polyethylene glycol-glycerol esters, polyethylene glycol phenols, polyethylene glycol-sorbitan fatty acid esters, polyglyceride fatty acids, polyoxyethylene-polyoxypropylene block copolymers, propylene glycol-fatty acid esters, sodium cholate, sodium lauryl sulfate, sodium palmitate, sodium taurocholate, sorbitan-fatty acid esters, sterol and sterol derivatives, sugar esters, transesterification products of oils and alcohols and mixtures thereof.

Examples of inorganic fillers include, but not limited to silicon dioxide, aluminum silicate, attapulgite, bentonite, calcium silicate, calcium carbonate, dicalcium phosphate, kaolin, lithium magnesium aluminum silicate, lithium magnesium silicate, lithium magnesium sodium silicate, magnesium silicate, magnesium trisilicate, montmorillonite, pyrophyllite, sodium magnesium silicate, talc, titanium dioxide, zeolite, and zirconium silicate, and mixtures thereof.

Examples of anti-adherents include, but not limited to, calcium carbonate, dicalcium phosphate, kaolin, talc, and titanium dioxide, and mixtures thereof.

Examples of erosion enhancers include, but not limited to, low molecular weight water soluble polymers such as hydroxyethyl cellulose, hydroxypropyl methyl cellulose, and polyvinyl pyrrolidone; polyols, such as mannitol, malitol, sorbitol, and xylytol, and surface active agents such as sodium lauryl sulfate, and Polysorbate 80, and mixtures thereof.

Examples of antioxidants include, but not limited to, butylhydroxytoulene, butylhydroxyanisole, propyl gallate, ascorbic acid and vitamin E-TPGS, and mixtures thereof.

Examples of buffering agents include, but not limited to, phosphates, citrates, acetates, oxides and carbonates, and mixtures thereof.

Process of Making the Erodible Tamper-Resistant Dosage Form

The erodible tamper-resistant dosage form of the present invention can be prepared according to the steps of:

(1) Blending at least one therapeutic agent and at least one substrate in a drug-to-substrate ratio from 1:20 to 20:1 by weight;

(2) Reacting the at least one therapeutic agent and the at least one substrate to form a therapeutic agent-substrate complex using a reactive extrusion process;

(3) Forming a thermo-formable matrix blend with at least one cellulosic thermoplastic polymer and optionally at least one non-cellulosic thermoplastic polymer, and at least one pharmaceutical additive;

(4) Mixing the therapeutic agent-substrate complex and the thermo-formable matrix blend in a ratio from 1:20 to 20:1 by weight;

(5) Granulating the therapeutic agent-substrate complex and the thermo-formable matrix blend to form the erodible tamper-resistant dosage form in which the therapeutic agent-substrate complex is embedded in the thermo-formable matrix;

(6) Shaping the tamper-resistant dosage form into one of tablet form and multiparticulate form, and (7) Optionally film-coating the tablets and multiparticulates.

The granulating step of (5) can be carried out by a hot melt extrusion process, or optionally by a wet granulation process or a dry granulation process.

The thermo-formable matrix imparts plasticity and hardness to the dosage form. Embedding the drug-substrate complex in the thermo-formable matrix produces a synergistic effect that renders the dosage form more resistant to tampering while releasing the therapeutic agent in a controlled manner. If only the therapeutic agent-substrate is used without the thermo-formable matrix during the preparation of extended release dosage forms, or if the therapeutic agent is dispersed in the thermo-formable matrix without a substrate, or if only a blend of the therapeutic agent and the substrate but not a complex is dispersed in the thermo-formable matrix the formulations do not exhibit both tamper-resistant and extended release properties.

Preparation of the Therapeutic Agent-Substrate Complex:

The therapeutic agent-substrate complex is prepared using a novel reactive extrusion process. The process is fast and continuous and more efficient compared to other commonly used processes. It allows the complexation process to proceed at a faster rate by providing flexibility in processing temperatures and online incorporation of pH modifiers and other additives that promote complex formation. As a result, the process has greater than 95% efficiency in the degree of complexation, a factor that is critical when considering the high cost of therapeutic agents. The extruder, which behaves as a reactor, is preferably a twin screw extruder. It comprises uniquely assembled conveying and mixing elements, and temperature controlled modular barrels that constitute a continuous reaction vessel. Along the extruder length, one or more liquid injection and powder feed ports are inserted in the barrels, wherein the number and location of the ports are dictated by the complexation process requirements.

During the complexation process, the drug and substrate are pre-blended and the blend introduced into the extruder through a powder feed port. At a second port downstream from the first feed port, an aqueous liquid is added at a controlled rate to generate a heavy suspension. The suspension is collected, dried in a drying oven and stored for further processing.

The ratio of the therapeutic agent to the substrate in the complex is from 1:50 to 50:1 by weight, preferably 1:20 to 20:1 and more preferably, from 1:10 to 10:1. The average particle size distribution of the substrate is less than 500 u (micron), preferably less than 250 u and more preferably, less than 75 u.

Alternatively, the complex may be prepared by a variety of processes known in the art.

Embedding Therapeutic Agent-Substrate Complex within Thermo Formable Matrix:

The therapeutic agent-substrate complex is blended with at least one cellulosic thermoplastic polymer and optionally at least one non-cellulosic thermoplastic polymer, or at least one pharmaceutical additive, or both, and the blend melt granulated at processing temperatures of less than 175° C. and preferably less than 150° C. using a twin-screw extruder. Alternatively, a blend of the thermoplastic polymers and optionally at least one pharmaceutical additive is fed into the extruder through the first powder feed port and allowed to melt before the therapeutic agent-substrate complex is introduced through a second powder feed port downstream from the first feed port and mixed with the molten mass in the extruder. In both procedures, the melt granulated material or extrudate is shaped downstream to provide tamper-resistant tablets or multiparticulates that are filled into capsules or compressed into tablets. The ratio of the therapeutic agent-substrate complex to the thermo-formable matrix varies, by weight, from 1:20 to 20:1, and preferably from 1:10 to 10:1, and more preferably from 1:5: to 5:1.

According to the disclosure, cellulosic thermoplastic polymers comprise, but not limited to, hydroxylpropyl cellulose, hydroxylpropyl methylcellulose, hydroxyethyl cellulose, and methylcellulose cellulose; and non-cellulosic thermoplastic polymers comprise, but not limited to, polyvinyl pyrrolidone, polyvinyl acetate polyvinyl alcohol, butyl/methyl methacrylate-dimethylaminoethylmethacrylate copolymer, polyethylene glycol, polyethylene oxide, polypropylene glycol and polyvinyl caprolactam-polyvinyl acetate-polyethylene glycol.

In one embodiment, the thermo-formable matrix comprises at least hydroxypropyl cellulose wherein the molecular weight is from 80,000 g/mol to 1,150,000 g/mol.

In another embodiment, the thermo-formable matrix comprises at least polyvinyl caprolactam-polyvinyl acetate-polyethylene glycol copolymer, wherein the molecular weight is 118,000 g/mol.

The yet another embodiment, the thermo-formable matrix comprises one or more substrates, including polyelectrolytes, inorganic adsorbents, inclusion compounds and fatty acids.

ADVANTAGES OF INVENTION

Resistance to Tampering

Tamper-resistance is achieved through a synchronized barrier mechanism composed of mechanical, physical and chemical components. According to the disclosure, hardness and plasticity is imparted onto the dosage form through a combination of thermal processing and the incorporation of uniquely blended water-soluble and water-insoluble polymers and other pharmaceutical additives in the formulation. As a result, the dosage form does not easily get plasticized during chewing and mastication. It instead hydrates, forms a thin gel layer and slowly erodes from the surface upon chewing or mastication while keeping the core dry and hard with limited liquid penetration. Similarly, the dosage form resists crushing, breaking and grinding using commonly used tools and hence does not generate fine powders suitable for snorting. Even grinding using a coffee grinder only produces coarse particles that are not suitable for snorting.

Moreover, even if the powders were suitable for snorting, which is not the case; the drug would not be available for absorption through the lining of the nasal cavity due to the complex and the rigid matrix in the particles.

Unique Mechanism of Drug Release

Without limiting the scope of this invention, the mechanism of how a drug is released from the erodible tamper-resistant dosage form can be illustrated by FIG. 1. According to the invention, the erodible tamper-resistant dosage form and the mechanism of release are applicable to either the tablet or the multiparticulate forms of the drug. As shown in FIG. 1, a tablet may be represented by a plurality of drug-substrate (DS) complexes, including prodrugs, imbedded in a matrix.

First, the tablet surface undergoes a hydration process that leads to the formation of a gel layer when a tablet is immersed in a dissolution medium or gastrointestinal fluid. Second, erosion of the gel layer takes place, leading to the release of the drug-substrate (DS) complexes. At this stage, the drug-substrate (DS) complexes are dislodged from the tablet and get suspended in the dissolution medium or gastrointestinal fluid. Third, the drug-substrate (DS) complexes are released into the dissolution or gastrointestinal fluid. Fourth, the free drug (D) is "decomplexed", that is, released from the drug-substrate (DS) complexes into the dissolution medium or gastrointestinal fluid through ionic displacement, enzymatic cleavage or pH effect. The release of the free drug (D) can be enhanced, for example, by the presence of an electrolyte (E), which associates with the substrate (S) to form an electrolyte-substrate (ES) complex.

According to the invention, drug release from the erodible tamper-resistant dosage form is controlled by (a) hardness of the dosage from which controls the rate of fluid penetration into the core, (b) composition of the dosage form which controls the strength, hydration rate and dissolution of the gel layer, and (c) the decomplexation process in the dissolution medium or gastrointestinal fluid. Such control as described in the present invention ensures that the dosage form would not be susceptible to dose dumping or food effect as is frequently observed with dosage forms that rely exclusively on matrix control for release.

Resistance to Extraction

Drug extraction from the dosage form is eliminated or minimized through a synchronized barrier mechanism. During the extraction process, the thermo-formable matrix generates a thin viscous gel layer on the surface over the hard and dry core of the dosage form, the thickness of which is dictated by the type of extraction solvent employed. In all cases, however, the drug-substrate complex present at the solvated gel layer cannot diffuse out into the extraction medium due to its poor mobility within the gel layer. Even if the thin gel layer were to erode and releases the drug-substrate complex into the extraction medium, the drug which, is tightly bound to the complex, and in turn "coated" by the thermoplastic polymer from the matrix, does not readily become available for extraction. This synchronized barrier mechanism comprising physical, mechanical and chemical components is a feature that differentiates the invention from prior art.

Figure 2A:
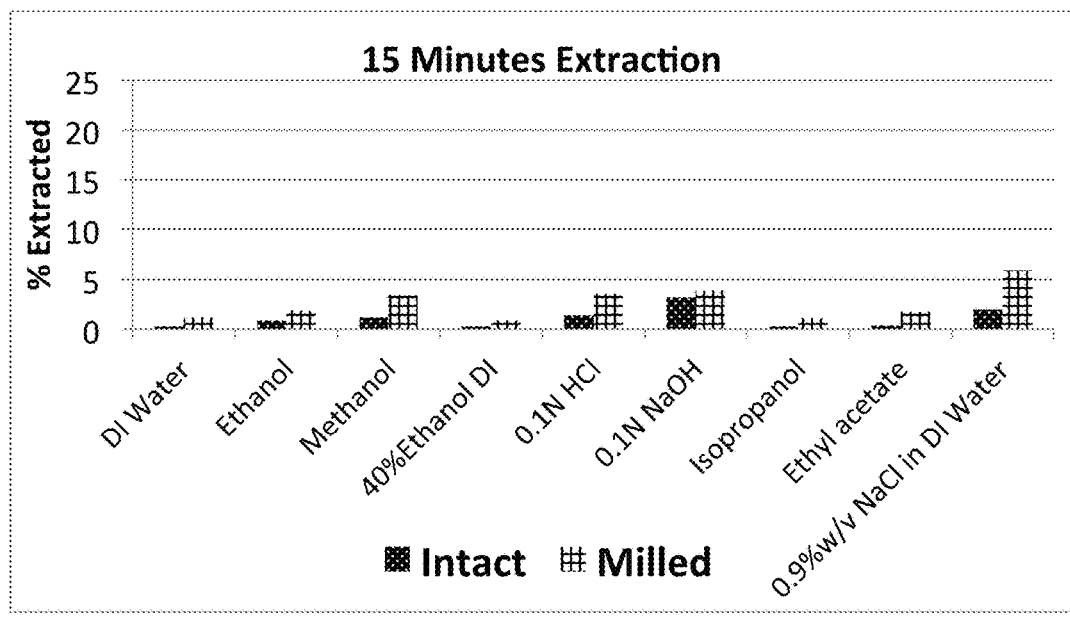
FIG. 2A shows 15-minute extraction of intact and milled tablets.
Figure 2B:
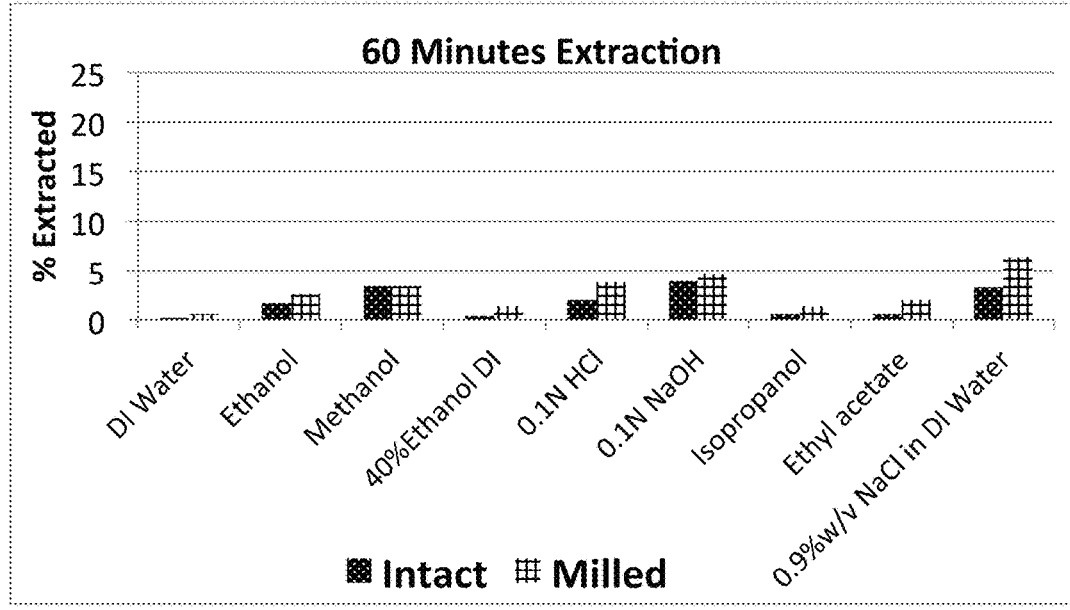
FIG. 2B shows 60-minute extraction of intact and milled tablets.

For example, extraction of the therapeutic agent using commonly used organic and household solvents with continuous agitation of the dosage form for at least 8 hours in 30 mL or 200 mL extraction volume leads to insignificant drug release. Similar results were obtained when the dosage form was milled in a coffee grinder and similarly tested for 15 minutes (as shown in FIG. 2A) and 60 minutes (as shown in FIG. 2B). In addition, it was discovered that when the milled particles were dissolved in an aqueous medium, they formed a viscous gel that trapped the complex, both of which made drug solubilization and syringeability impossible.

Examples of prescription drugs abused by injection include: barbiturates, such as phenobarbital and secobarbital; opioids such as morphine, codeine, fentanyl, methadone, oxycodone HCl, hydrocodone bitartrate, hydromorphone, oxymorphone, meperidine and propoxyphene; stimulants such as amphetamine and methylphenidate.

Resistance to Vaporization

Abusers often heat the dosage forms to vaporize the drug for smoking purposes. According to the invention, vaporization of a drug from the dosage form is prevented through density and hardness of the dosage form, immobilization of the drug within the drug-substrate complex, and immobilization of the drug-substrate complex within the thermo-formable matrix. The drug-substrate complex has much lower vapor pressure than that of the free drug, and, as a result, requires much higher heat energy to liberate the free drug from the complex and the matrix, if the dosage form were thermally stable when exposed to elevated temperatures. However, it was discovered that excessive heating of the dosage form leads to decomposition and charring of formulation components, which potentially liberate obnoxious fumes that the abuser may not tolerate.

For example, the dosage form is placed on top of a spoon, and heated from underneath using a cigarette lighter or high temperature acetylene torch to vaporize the therapeutic agent. Excessive heating of the dosage form leads to decomposition and charring of formulation components. Examples of prescription drugs abused by smoking include: fentanyl and its analogs, amphetamines, and morphine.

Resistance to Chewing, Crushing and Milling

The dosage form is also resistant to chewing irrespective of the bite force applied. It only erodes over time. The eroded material still contains the drug-substrate complex "coated" by the matrix components which would prevent immediate drug absorption upon ingestion. Examples of prescription drugs abused by swallowing include; barbiturates such as phenobarbital and secobarbital; opioids such as morphine, codeine, fentanyl, methadone, oxycodone HCl, hydrocodone bitartrate, hydromorphone, oxymorphone, meperidine, propoxyphene and dextromethorphan; benzodiazepines such as diazepam and clonazepam; sleep medications such as zolpidem and zaleplon; and stimulants such as amphetamine and methylphenidate.

The dosage form is resistant to crushing and milling even if a substantial force is applied. Milling or grinding the dosage form into fine powder using conventional methods, such as mortar and pestle or a hammer mill is impossible; milling using a coffee grinder is possible, although the dosage form does not get reduced into fine powder that would allow the abuser to administer the therapeutic agent intra-nasally to facilitate drug absorption through the lining of the nasal passages by snorting. Even if the dosage from were susceptible to produce fine powders upon pulverization, which is not the case, the therapeutic agent would still be tightly bound to the substrate and "coated" by the thermoplastic polymer, and not become available for intra-nasal absorption. Examples of prescription drugs abused by snorting include: opioids such as morphine, codeine, fentanyl, methadone, oxycodone HCl, hydrocodone bitartrate, hydromorphone, oxymorphone, meperidine and propoxyphene; sleep medications such as zolpidem and zaleplon; stimulants such as amphetamine and methylphenidate.

Ingestion of Multiple Tablets

Figure 3:
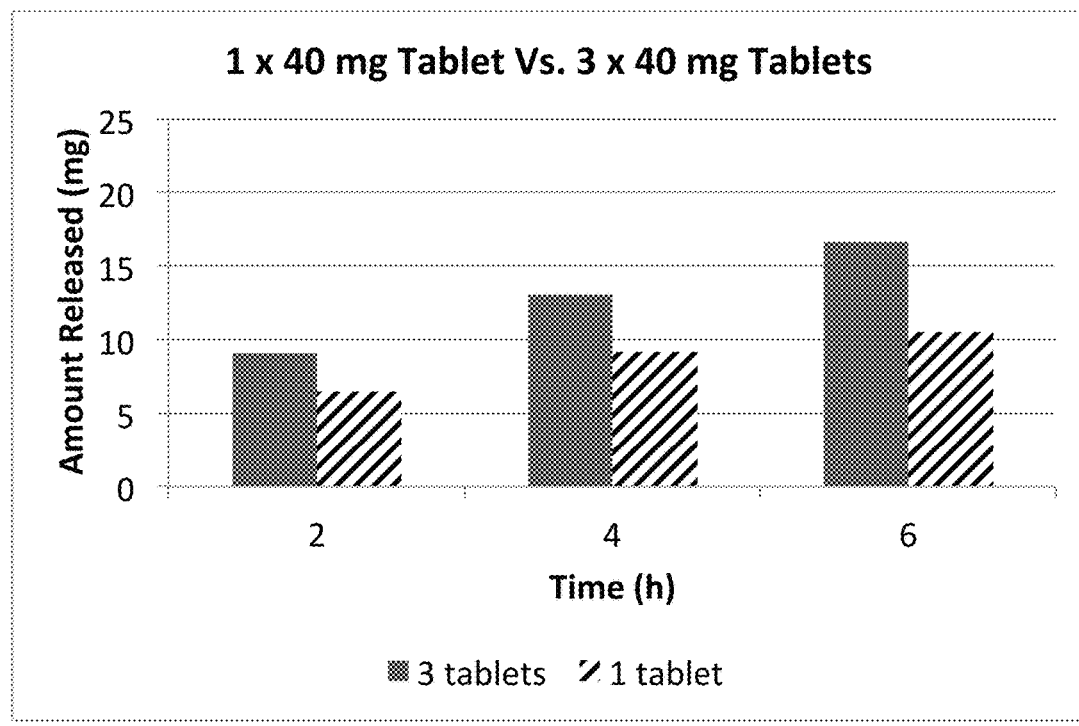
FIG. 3 shows the self-limiting drug release when multiple tablets are taken.

In yet another embodiment, the present invention relates to a dosage form that potentially prevents drug abuse by ingestion of multiple tablets. The amount of drug released from multiple tablets in simulated gastrointestinal fluid relative to a single unit is greatly reduced and is not dose proportional (FIG. 3). It is expected that the spike desired by abusers would not occur when more units than required by dosing instructions are ingested by the abusers.

Versatile Modified Formulations

Figure 4:
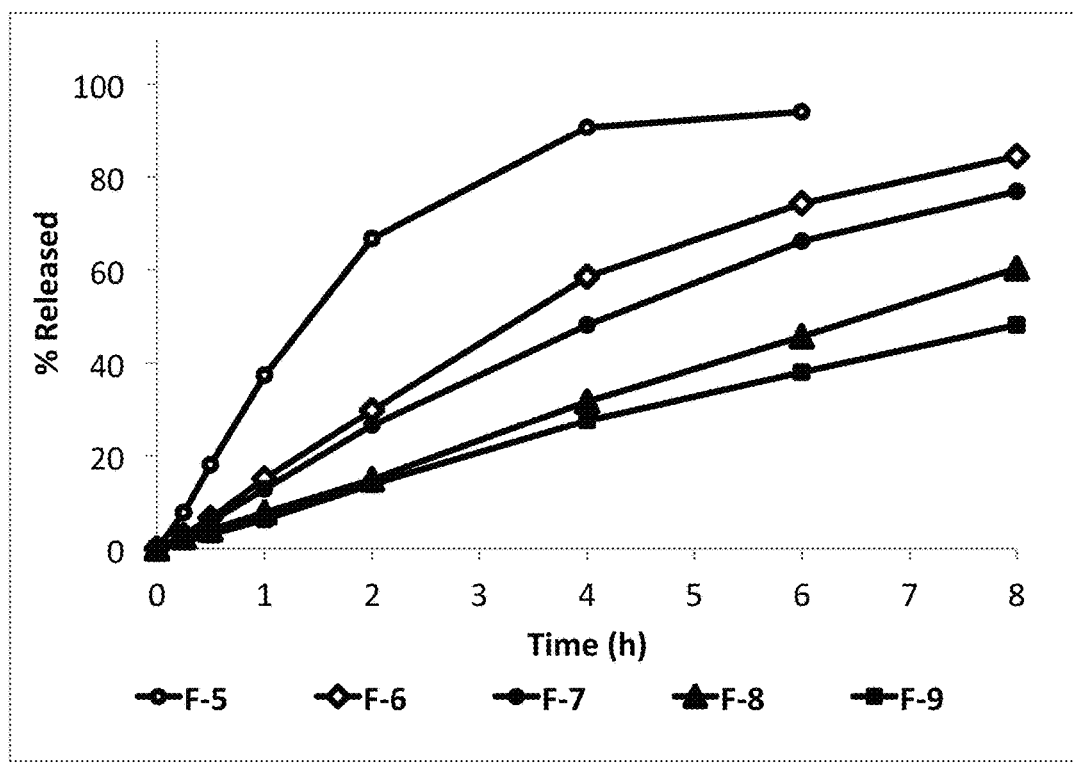
FIG. 4 shows the dissolution profiles of multiple tamper-resistant template tablet formulations.

In yet another embodiment, the present invention relates to formulations that provide multiple modified release profiles. For example, the profiles of five different formulations, F5, F6, F7, F8 and F9, which range from over 90% in 4 hours to greater than 90% in 24 hours (FIG. 4), demonstrate the flexibility of the formulations and the opportunity they provide during the development of dosage forms that satisfy the diverse pharmacokinetic requirements of therapeutic agents.

Drug Independent Formulations

Figure 5:
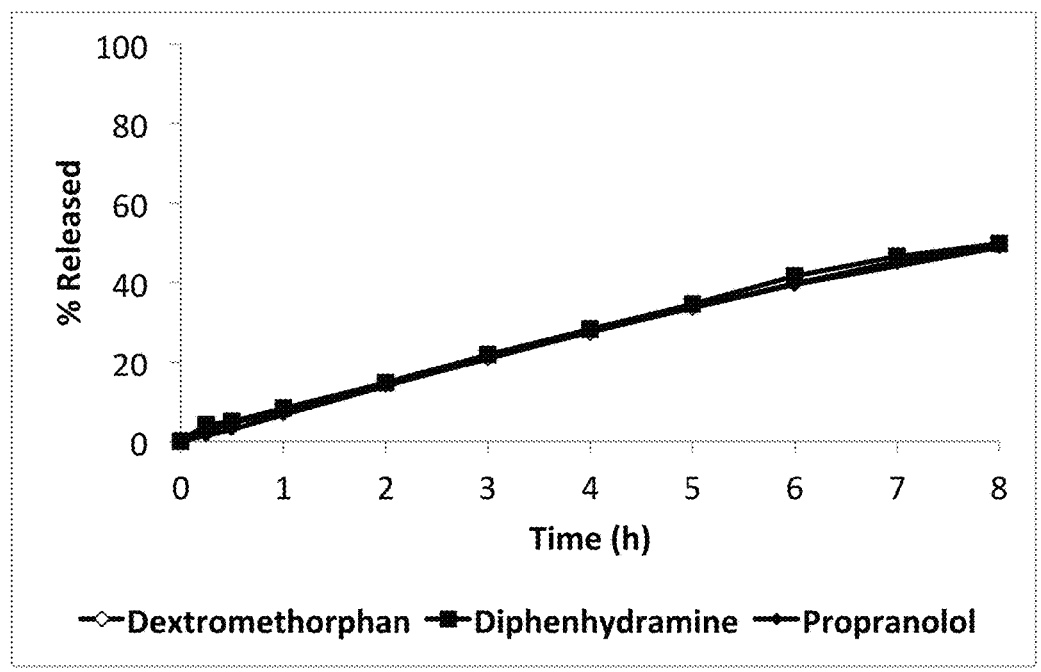
FIG. 5 shows the dissolution profiles of three different therapeutic agents in the same template tamper-resistant tablet formulation.

In yet another embodiment, the present invention relates to a dosage form that generates release rates that are independent of therapeutic agents. That is, different therapeutic agents incorporated in a given formulation provide the same release profiles. Such a surprising discovery makes it possible to establish base formulations (templates) that would form the basis for the development of different products, thereby shortening development time (FIG. 5).

Ensuring Chemical Stability and Increasing Shelf Life

In yet another embodiment, the present invention relates to a dosage form that increases the shelf life of products by eliminating or at least minimizing oxidative or hydrolytic decomposition of therapeutic agents. Many therapeutic agents, including opioids, undergo oxidative or hydrolytic degradation when exposed to acidic or alkaline aqueous environments or thermal stresses, or both. Moreover, some pharmaceutical additives, such as polyethylene oxide, contain trace amounts of peroxides and promote oxidation of the therapeutic agent upon storage or during thermal processing, and, as a result, anti-oxidants and buffering agents are routinely added to formulations to prevent potential degradation of therapeutic agents through the shelf-life of the dosage forms. In the present invention, the formation and incorporation of the drug-substrate complex within the thermo-formable matrix generally obviates the need for incorporating anti-oxidants and buffering agents in the dosage form (as illustrated by formulations F23, F41, F46 and F64 in FIG. 6), although incorporation of these agents is also possible in special cases.

Ensuring Dissolution Stability and Shelf Life

Figure 7:
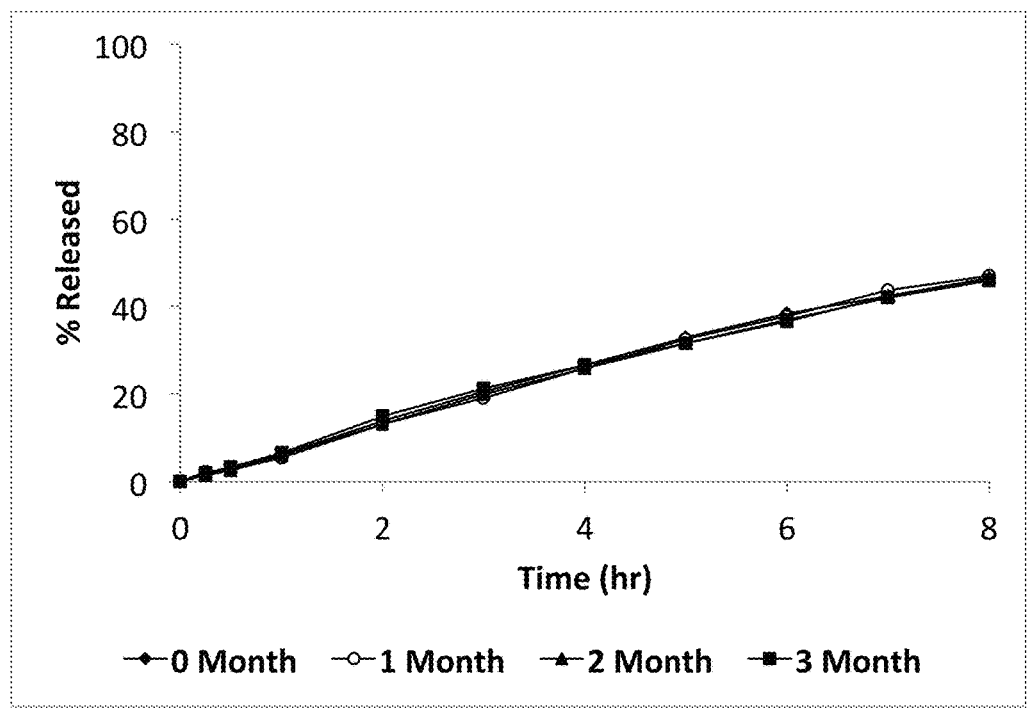
FIG. 7 shows the 3-month accelerated dissolution stability.

In yet another embodiment, the invention relates to a tamper-resistant dosage form that ensures dissolution stability and consequently the shelf-life of products. The dissolution stability of matrix-based dosage forms is dictated by the rate of migration of the drug molecules within the matrix which in turn depends on the physical stability of the matrix and the properties of the drug substance. Changes in the physical stability of the matrix retards or accelerates the migration of the drug molecules, which in turn affect release rate. In contrast, according to the current invention, mobility of the drug-substrate complex is restricted within the matrix, thereby enhancing dissolution stability of the dosage form (as illustrated by the % released profiles over a 3-month period in FIG. 7).

Multiparticulates Compressed into Tablets

Figure 8:
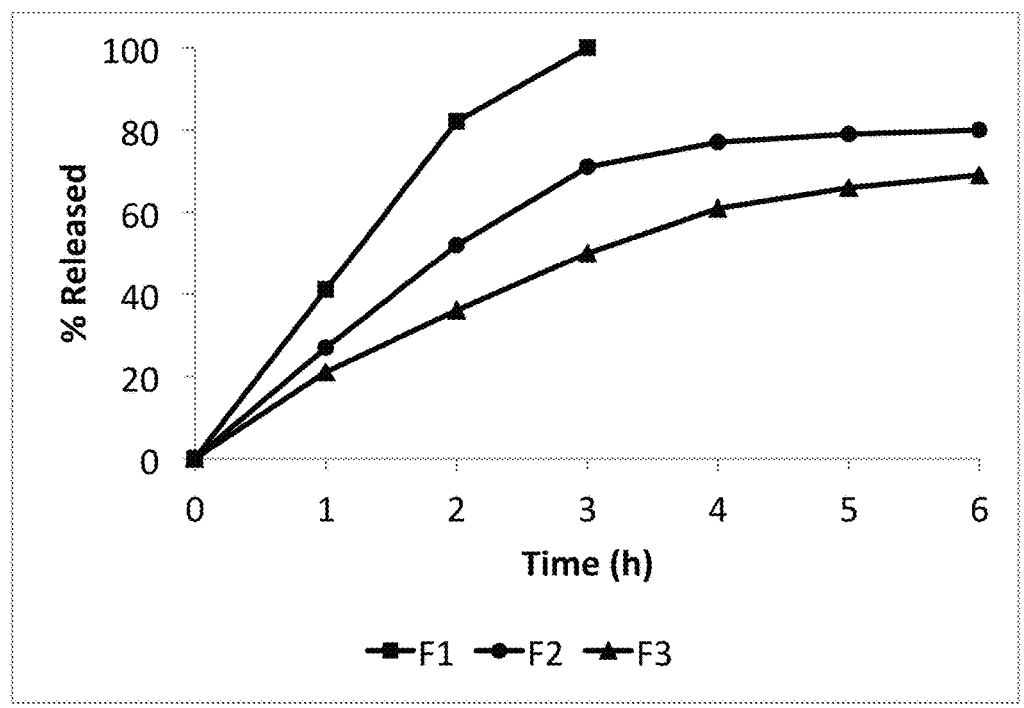
FIG. 8 shows the dissolution profiles of tamper-resistant multiparticulates compressed into tablets.

In yet another embodiment, the invention relates a tamper-resistant dosage form comprising multi-particulates that are compressed into tablets. Multiparticulates are blended with other tableting excipients and compressed. During dissolution, the compressed tablets disintegrate in less than a minute to regenerate the original multiparticulates, and release the therapeutic agent completely from less than an hour to up to 24 hours. For example, three different compressed multiparticulate formulations, F1, F2 and F3, released 50%, 71% and 100% of the drug, respectively, at the 3-hour time point (FIG. 8).

EXAMPLES

The following examples are included to demonstrate certain embodiments of the present invention and not intended to be limiting. They are for illustrative purposes only and it is to be noted that changes and variations can be made without departing from the spirit and scope of the invention.

Example 1

Preparation of Drug-Substrate Complex

In this example, a general process for the preparation of a drug-substrate complex is illustrated using an ion exchange resin as a model substrate. For example, a drug-ion exchange resin complex is prepared from a blend of the drug and Amberlite IRP 69 (Sodium polystyrene sulfonate, manufactured by Rohm Haas, Philadelphia, Pa., USA and supplied by Dow Chemical Company, Midland, Mich., USA) using a novel reactive extrusion process. A 16 mm twin-screw extruder is used as a reactor, although larger size extruders could be used if the desired batch size is high. The drug and Amberlite IRP 69 are pre-blended and the blend introduced into the extruder through a powder feed port. At a second port downstream from the first feed port, deionized water is added at a controlled rate to generate a heavy suspension. The extrusion process is carried out at a screw speed of 300 rpm and processing temperatures of 25° C. The suspension is collected, dried in a drying oven and stored for further processing.

Alternatively, the suspension is washed using deionized water to remove any free uncomplexed drug as is done with other methods known in the art. The supernatant is decanted and discarded. The residue comprising a drug-ion exchange resin complex is then dried in a drying oven.

Example 2

Propranolol Ion-Exchange Resin Complex Particles

A formulation composed of a complex of a therapeutic agent (propranolol), and a substrate (ion-exchange resin) only, without the incorporation of a thermoplastic polymer, and hence a thermoformable matrix, was prepared. The propranolol ion exchange resin complex was prepared using the procedure described in Example 1.

Dissolution Studies:

Dissolution studies were conducted in 900 mL of pH 6.8 Phosphate buffer (0.05M) consisting of 0.2% sodium chloride using USP Apparatus II (Paddle) at 75 rpm. The dissolution data is given below:

| Time (h) | % Released |
|---|---|
| 0.25 | 78 |
| 0.5 | 89 |
| 1 | 96 |
| 2 | 98 |

Extraction Studies

Extraction studies were conducted in different solvents using a wrist action shaker at a speed of 416 rpm and 18° angle. Samples were withdrawn at 15 minutes and 60 minutes and the drug release was determined using a spectrophotometer. The results are given below:

| Extraction Solvent | % Released 15 min | % Released 60 min |
|---|---|---|
| 0.9% NaCl solution | 3.4 | 3.6 |
| Methanol | 0.4 | 0.5 |
| Water | 0.5 | 0.4 |
| 0.1N HCl | 1.4 | 1.4 |
| Ethanol 40% | 0.4 | 0.4 |
| 0.1N NaOH | 2.7 | 2.5 |
| Ethanol 96% | 0.2 | 0.2 |
| Isopropanol | 0.6 | 0.8 |
| Ethylacetate | 0.2 | 0.2 |

Example 3

Propranolol HCl Multiparticulates

A formulation composed of a therapeutic agent (propranolol), thermoplastic polymers (hydroxypropylcellulose I and II) and a pharmaceutical additive (silicon dioxide) was prepared. Neither a substrate, nor a therapeutic agent-substrate complex was included in the formulation.

Propranolol HCl (free drug), hydroxypropylcellulose (I), hydroxypropylcellulose (II) and silicon dioxide were blended, fed into a 16 mm twin screw extruder and extruded. The extrusion process was carried out at a processing temperature of 140° C. and a screw speed of 200 rpm. The extrudates were shaped into multiparticulates downstream. A portion of the multiparticulates were mixed with external excipients and compressed into tablets. The tablets and the remaining portion of multiparticulates were collected and stored in high density polyethylene (HDPE) bottles.

| Ingredient | % w/w |
|---|---|
| Propranolol HCl | 25 |
| Hydroxypropyl cellulose (I) (M.W. 370,000) | 35.5 |
| Hydroxypropyl cellulose (II) (M.W. 80,000) | 35.5 |
| Silicon dioxide | 4 |
| Total | 100 |

Dissolution Studies:

Dissolution studies were conducted in pH 6.8 Phosphate buffer (0.05M) consisting of 0.2% sodium chloride using USP Apparatus II (Paddle) at 75 rpm. The tablets disintegrated within 1 minute in the dissolution medium. The dissolution data is given below:

| Time (h) | % Released |
|---|---|
| 0.25 | 41 |
| 0.5 | 69 |
| 1 | 100 |

Extraction Studies

Extraction studies were conducted in different solvents using a wrist action shaker at a speed of 416 rpm and 18° angle. Samples were withdrawn at 15 minutes and 60 minutes and drug release determined using a spectrophotometer. The results are given below:

| Extraction Solvent | % Released 15 min | % Released 60 min |
|---|---|---|
| 0.9% NaCl solution | 62.6 | 94.2 |
| Methanol | 94.7 | 99.3 |
| Water | 77.4 | 94.2 |
| 0.1N HCl | 68.7 | 90.8 |
| Ethanol 40% | 42.4 | 85.9 |
| 0.1N NaOH | 4.3 | 5.0 |
| Ethanol 96% | 42.8 | 80.7 |
| Isopropanol | 22.5 | 44.1 |
| Ethylacetate | 23.4 | 25.4 |

Example 4

Propranolol HCl and Ion-Exchange Resin Blend-Based Multiparticulates

A formulation composed of a therapeutic agent (propranolol), a substrate (Amberlite IRP 69), thermoplastic polymers (hydroxypropylcellulose I and II) and a pharmaceutical additive (silicon dioxide) was prepared. The therapeutic agent and the substrate were incorporated in the formulation independently and not as a pre-formed complex.

Propranolol HCl (free drug), Amberlite IRP 69 (uncomplexed resin), hydroxypropylcellulose (I), hydroxypropylcellulose (II) and silicon dioxide were blended, fed into a 16 mm twin screw extruder and extruded. The extrusion process was carried out at processing temperatures of 140° C. and a screw speed of 200 rpm. The extrudates were shaped into multiparticulates downstream. A portion of the multiparticulates were mixed with external excipients and compressed into tablets. The tablets and the remaining portion of the multiparticulates were collected and stored in high density polyethylene (HDPE) bottles.

| Ingredient | % w/w |
|---|---|
| Propranolol HCl | 25 |
| Amberlite IRP 69 (Ion-exchange resin) | 25 |
| Hydroxypropyl cellulose (I) (M.W. 370,000) | 23 |

-continued

| Ingredient | % w/w |
|---|---|
| Hydroxypropyl cellulose (II) (M.W. 80,000) | 23 |
| Silicon dioxide | 4 |
| Total | 100 |

Dissolution Studies:

Dissolution studies were conducted in pH 6.8 Phosphate buffer (0.05M) consisting of 0.2% sodium chloride using USP Apparatus II (Paddle) at 75 rpm. The tablets disintegrated within 1 minute in the dissolution medium. The dissolution data is given below:

| Time (h) | % Released |
|---|---|
| 0.25 | 43 |
| 0.5 | 63 |
| 1 | 93 |
| 2 | 100 |

Extraction Studies

Extraction studies were conducted on the multiparticulates in different solvents using a wrist action shaker at a speed of 416 rpm and 18° angle. Samples were withdrawn at 15 minutes and 60 minutes and the drug release was determined using a spectrophotometer. The results are given below:

| | % Released | |
|---|---|---|
| Extraction Solvent | 15 min | 60 min |
| 0.9% NaCl solution | 45.6 | 58.3 |
| Methanol | 75.4 | 77.6 |
| Water | 54.5 | 57.2 |
| 0.1N HCl | 41.2 | 40.6 |
| Ethanol 40% | 44.6 | 45.1 |
| 0.1N NaOH | 5.7 | 5.4 |
| Ethanol 96% | 64.8 | 69.5 |
| Isopropanol | 36.4 | 55.2 |
| Ethylacetate | 9.3 | 12.3 |

Example 5

Propranolol Ion-Exchange Resin Complex-Based Multiparticulates

A formulation composed of a therapeutic agent-substrate complex (Propranolol-Amberlite IRP 69 complex), thermoplastic polymers (hydroxypropylcellulose I and II) and a pharmaceutical additive (silicon dioxide) was prepared.

Propranolol ion exchange complex, hydroxypropylcellulose (I), hydroxypropylcellulose (II) and silicon dioxide were blended, fed into a 16 mm twin screw extruder and extruded. The extrusion process was carried out at a processing temperature of 140° C. and a screw speed of 200 rpm. The extrudates were shaped into multiparticulates downstream. A portion of the multiparticulates were mixed with external excipients and compressed into tablets. The tablets and the remaining portion of multiparticulates were collected and stored in high density polyethylene (HDPE) bottles.

| Ingredient | % w/w |
|---|---|
| Propranolol Ion Exchange Resin Complex | 50 |
| Hydroxypropyl cellulose (I) (M.W. 370,000) | 23 |
| Hydroxypropyl cellulose (II) (M.W. 80,000) | 23 |
| Silicon dioxide | 4 |
| Total | 100 |

Dissolution Studies:

Dissolution studies were conducted in pH 6.8 Phosphate buffer (0.05M) consisting of 0.2% sodium chloride using USP Apparatus II (Paddle) at 75 rpm. The tablets disintegrated within 1 minute in the dissolution medium. The dissolution data is given below:

| Time (h) | % Released |
|---|---|
| 0.25 | 0.5 |
| 0.5 | 4 |
| 1 | 13 |
| 2 | 35 |
| 3 | 62 |
| 4 | 77 |

Extraction Studies

Extraction studies were conducted in different solvents using a wrist action shaker at a speed of 416 rpm and 18° angle. Samples were withdrawn at 15 minutes and 60 minutes and the drug release was determined using a spectrophotometer. The results are given below:

| | % Released | |
|---|---|---|
| Extraction Solvent | 15 min | 60 min |
| 0.9% NaCl solution | 3.1 | 4.5 |
| Methanol | 2.3 | 2.6 |
| Water | 0.9 | 3.4 |
| 0.1N HCl | 1.5 | 2.1 |
| Ethanol 40% | 1.0 | 1.1 |
| 0.1N NaOH | 5.5 | 5.7 |
| Ethanol 96% | 1.9 | 5.0 |
| Isopropanol | 1.0 | 2.5 |
| Ethylacetate | 0.7 | 1.2 |

Example 6

Dextromethorphan-Ion Exchange Resin Complex-Based Tablets

A mixture of Dextromethorphan ion exchange resin complex, hydroxypropylcellulose (I), hydroxypropylcellulose (II) and polyethylene glycol were blended and fed into a 16 mm twin screw extruder and extruded at extrusion temperatures of 100° C. and a screw speed of 200 rpm. The extrudate was shaped into tablets downstream. The tablets were collected and stored in high density polyethylene (HDPE) bottles.

| Ingredient | % w/w |
|---|---|
| Dextromethorphan Ion Exchange Resin Complex | 50 |
| Hydroxypropyl cellulose (I) (M.W. 370,000) | 26.25 |
| Hydroxypropylcellulose (II) (M.W. 80,000) | 8.75 |
| Polyethylene glycol (M.W. 400) | 15 |
| Total | 100 |

Dissolution Studies:

Dissolution studies were conducted in pH 6.8 Phosphate buffer (0.05M) consisting of 0.2% sodium chloride using USP Apparatus I (basket) at 100 rpm. The dissolution data is given below:

| Time (h) | % Released |
|---|---|
| 1 | 7 |
| 2 | 15 |
| 3 | 21 |
| 4 | 28 |
| 5 | 34 |
| 6 | 40 |
| 7 | 45 |
| 8 | 49 |

Extraction Studies

Extraction studies were conducted in different solvents using a wrist action shaker at a speed of 416 rpm and 18° angle. Samples were withdrawn at 15 minutes and 60 minutes, and the drug release was determined using a UV-spectrophotometer. The results are given below:

| | Intact Tablets | |
|---|---|---|
| | % Released | |
| Extraction Solvent | 15 min | 60 min |
| Methanol | 1.2 | 2.3 |
| Water | 0.2 | 0.3 |
| 0.1N HCl | 1.7 | 2.7 |
| Ethanol 40% | 0.5 | 0.7 |
| 0.1N NaOH | 6.9 | 6.2 |
| Ethanol 96% | 0.7 | 1.5 |
| Isopropanol | 0.3 | 0.6 |
| Ethylacetate | 0.3 | 0.7 |

The data indicates that the invention permits the preparation of dextromethorphan tablets that have extended release dissolution profiles and at the same time provide tamper resistance as demonstrated by the low level of extractability of the therapeutic agent from the tablets using different extraction solvents.

Example 7

Propranolol-Ion Exchange Tablets

Two different formulations (F-3 and F-4) containing Propranolol-Ion exchange resin complex were blended and fed into a 16 mm twin screw extruder and extruded at processing temperatures of 100° C. and screw speed of 200 rpm. The extrudates were shaped into tablets in a downstream processing step. The tablets were collected and stored in high density polyethylene (HDPE) bottles.

| | % w/w | |
|---|---|---|
| Ingredient | F-3 | F-4 |
| Propranolol Ion Exchange Resin Complex | 50 | 50 |
| Hydroxypropylcellulose (I) (M.W. 370,000) | 26.25 | 8.75 |
| Hydroxypropylcellulose (II) (M.W. 80,000) | 8.75 | 26.25 |
| Polyethylene glycol (M.W. 400) | 15 | 15 |
| Total | 100 | 100 |

Dissolution Studies:

Dissolution studies were conducted on the tablets using USP Apparatus I (Basket) at 100 rpm in pH 6.8 Phosphate buffer (0.05M) consisting of 0.2% sodium chloride. The dissolution data is given in the table below:

| | % Released | |
|---|---|---|
| Time (h) | F-3 | F-4 |
| 1 | 7 | 15 |
| 2 | 14 | 30 |
| 4 | 28 | 59 |
| 6 | 40 | 74 |
| 8 | 49 | 84 |

Extraction Studies

Extraction studies were conducted on the tablets in different solvents using a wrist action shaker at a speed of 416 rpm and 18° angle. Samples were withdrawn at 15 minute and 60 minute time intervals and drug release was measured using a UV-spectrophotometer. The extraction results are given below:

| | Extraction of Intact Tablets % Released | | | |
|---|---|---|---|---|
| | F-3 | | F-4 | |
| Extraction Solvent | 15 min | 60 min | 15 min | 60 min |
| Methanol | 0.9 | 1.9 | 1.6 | 3.4 |
| Water | 0.1 | 0.2 | 0.2 | 0.4 |
| 0.1N HCl | 1.0 | 1.4 | 1.1 | 1.5 |
| Ethanol 40% | 0.3 | 0.5 | 0.3 | 0.7 |
| 0.1N NaOH | 1.8 | 2.1 | 2.2 | 2.2 |
| Ethanol 96% | 0.3 | 1.0 | 0.8 | 1.6 |
| Isopropanol | 0.3 | 0.8 | 0.3 | 0.6 |
| Ethylacetate | 0.3 | 0.7 | 0.3 | 0.6 |

The data demonstrates that the invention permits the development of different Propranolol-ion exchange formulations that have different dissolution profiles and at the same time provide similar tamper resistant properties as demonstrated by the low level of extractability of the therapeutic agent from the tablets.

Example 8

Propranolol-Ion Exchange Tablet Formulations with an Erosion Enhancer

Two different Propranolol-ion exchange complex formulations (F-5 and F-6) containing an erosion enhancer were blended and fed into a 16 mm twin screw extruder and extruded at processing temperatures of 100° C. and screw speed of 200 rpm. The extrudates were shaped into tablets in a downstream processing step. The tablets were collected and stored in high density polyethylene (HDPE) bottles.

| Ingredient | % w/w | |
|---|---|---|
| | F-5 | F-6 |
| Propranolol Ion Exchange Resin Complex | 50 | 50 |
| Hydroxypropylcellulose (I) (M.W. 370,000) | 18.4 | 15.75 |
| Hydroxypropylcellulose (II) (M.W. 80,000) | 6.1 | 5.25 |
| Polyethylenoxide (M.W. 200,000) | 10.5 | 14 |
| Polyethylene glycol (M.W. 400) | 15 | 15 |
| Total | 100 | 100 |

Dissolution Studies:

Dissolution studies were conducted on the tablets using USP Apparatus I (Basket) at 100 rpm in pH 6.8 Phosphate buffer (0.05M) consisting of 0.2% sodium chloride. The dissolution data is given below:

| Time (h) | % Released | |
|---|---|---|
| | F-5 | F-6 |
| 1 | 12 | 12 |
| 2 | 22 | 25 |
| 4 | 39 | 47 |
| 6 | 50 | 64 |
| 8 | 58 | 73 |

Extraction Studies

Extraction studies were conducted on intact tablets in different solvents using a wrist action shaker at a speed of 416 rpm and 18° angle. Samples were withdrawn at 15 minutes and 60 minutes, and drug release was measured using a UV-spectrophotometer. The results are given below:

| | Extraction of Intact Tablets % Released | | | |
|---|---|---|---|---|
| | F-5 | | F-6 | |
| Extraction Solvent | 15 min | 60 min | 15 min | 60 min |
| Methanol | 0.5 | 1.6 | 1.1 | 2.8 |
| Water | 0.1 | 0.2 | 0.2 | 0.4 |
| 0.1N HCl | 0.9 | 1.3 | 1.5 | 1.9 |
| Ethanol 40% | 0.2 | 0.5 | 0.4 | 0.8 |
| 0.1N NaOH | 2.5 | 2.1 | 3.1 | 2.6 |
| Ethanol 96% | 0.3 | 0.7 | 0.5 | 1.1 |
| Isopropanol | 0.3 | 0.5 | 0.4 | 0.9 |
| Ethylacetate | 0.3 | 0.5 | 0.2 | 0.4 |

The above examples illustrate that release profiles of dosage forms can be modified using erosion enhancers without compromising the tamper resistance properties of the dosage forms.

Example 9

Propranolol-Ion Exchange Tablet Formulations with a Viscosity Enhancer

A mixture of Propranolol ion exchange resin complex, hydroxypropylcellulose (I), hydroxypropylcellulose (II), polyethylene oxide, polyethylene glycol and silicon dioxide were blended and fed into a 16 mm twin screw extruder and extruded at extrusion temperatures of 140° C. and a screw speed of 200 rpm. The extrudate was shaped into tablets downstream. The tablets were collected and stored in high density polyethylene (HDPE) bottles.

| Ingredient | % w/w |
|---|---|
| Propranolol Ion Exchange Resin Complex | 50 |
| Hydroxypropylcellulose (I) (M.W. 370,000) | 8.6 |
| Hydroxypropylcellulose (II) (M.W. 80,000) | 26.1 |
| Polyethylene Oxide (M.W. 4,000,000) | 8.6 |
| Polyethylene glycol (M.W. 400) | 4.8 |
| Silicon dioxide | 1.9 |
| Total | 100 |

Dissolution Studies:

Dissolution studies were conducted on the tablets using USP Apparatus I (Basket) at 100 rpm in pH 6.8 Phosphate buffer (0.05M) consisting of 0.2% sodium chloride. The dissolution data is given below:

| Time (h) | % Released |
|---|---|
| 1 | 9 |
| 2 | 19 |
| 3 | 29 |
| 4 | 38 |
| 5 | 46 |
| 6 | 55 |
| 7 | 61 |
| 8 | 65 |

Extraction Studies

Extraction studies were conducted on the tablets in different solvents using a wrist action shaker at a speed of 416 rpm and 18° angle. Samples were withdrawn at 15 minute and 60 minute time intervals and drug release was measured using a UV-spectrophotometer. The extraction results are given below:

| | Extraction of Intact Tablets | |
|---|---|---|
| Extraction | % Released | |
| Solvent | 15 min | 60 min |
| Methanol | 2.0 | 3.4 |
| Water | 0.3 | 0.5 |
| 0.1N HCl | 1.4 | 2.0 |
| Ethanol 40% | 0.4 | 0.8 |
| 0.1N NaOH | 2.4 | 2.9 |
| Ethanol 96% | 0.7 | 1.4 |
| Isopropanol | 0.6 | 0.8 |
| Ethylacetate | 0.3 | 0.5 |

The data demonstrates that the invention permits the development of Propranolol-ion exchange formulations that contain viscosity enhancing polymer and at the same time provide similar tamper resistant properties as demonstrated by the low level of extractability of the therapeutic agent from the tablets.

Example 10

Propranolol Tablet Formulations Manufactured by Dry Granulation

A mixture of Propranolol ion exchange resin complex, hydroxypropyl methyl cellulose K100M CR (I), Lactose, PVP K30 and stearic acid were blended, dry granulated, milled and compressed. Tablets were collected and stored in high density polyethylene (HDPE) bottles.

| Ingredient | % w/w |
|---|---|
| Propranolol Ion Exchange Resin Complex | 50 |
| Hydroxypropylmethyl cellulose K100 M CR | 30 |
| Lactose | 10 |
| PVP K30 | 9.5 |
| Stearic acid | 0.5 |
| Total | 100 |

Dissolution Studies:

Dissolution studies were conducted using USP Apparatus II (Paddle) at 100 rpm in pH 6.8 Phosphate buffer (0.05M) consisting of 0.2% sodium chloride. The dissolution data is given below

| Time (h) | % Released |
|---|---|
| 0 | 0 |
| 1 | 11 |
| 2 | 20 |
| 3 | 27 |
| 4 | 33 |
| 5 | 38 |
| 6 | 45 |
| 7 | 51 |
| 8 | 56 |

Extraction studies were conducted in different solvents using a wrist action shaker at a speed of 416 rpm and 18° angle. Samples were withdrawn at 15 minutes and 60 minutes and the drug release was determined using a spectrophotometer. The results are given below:

| | % Released | |
|---|---|---|
| Extraction Solvent | 15 min | 60 min |
| Methanol | 3.0 | 3.2 |
| 0.1N HCl | 2.9 | 3.1 |
| 0.1N NaOH | 6.7 | 8.0 |
| Ethylacetate | 1.1 | 1.8 |

Example 11

Propranolol Tablet Formulations Manufactured by Wet Granulation

A mixture of Propranolol ion exchange resin complex, hydroxypropylmethyl cellulose LVCR CR (I), and Polyethylen oxide, PVP K30 were blended and wet granulated. The granulation was dried in forced air oven at 40° C. overnight and delumped by passing through a screen. The milled granulation was then compressed in to appropriate tablet size. Tablets were collected and stored in high density polyethylene (HDPE) bottles.

| Ingredient | % w/w |
|---|---|
| Propranolol Ion Exchange Resin Complex | 50 |
| Hydroxypropylmethyl cellulose LV CR | 40 |
| Polyethylenoxide (M.W. 200,000) | 10 |
| Total | 100 |

Dissolution Studies:

Dissolution studies were conducted using USP Apparatus II (Paddle) at 100 rpm in pH 6.8 Phosphate buffer (0.05M) consisting of 0.2% sodium chloride. The dissolution data is given below:

| Time (h) | % Released |
|---|---|
| 0 | 0 |
| 1 | 6 |
| 2 | 14 |
| 3 | 22 |
| 4 | 31 |
| 5 | 44 |
| 6 | 55 |
| 7 | 71 |
| 8 | 82 |

Extraction studies were conducted in different solvents using a wrist action shaker at a speed of 416 rpm and 18° angle. Samples were withdrawn at 15 minutes and 60 minutes and the drug release was determined using a spectrophotometer. The results are given below:

| | % Released | |
|---|---|---|
| Extraction Solvent | 15 min | 60 min |
| Methanol | 8.2 | 9.5 |
| 0.1N HCl | 3.5 | 4.4 |
| 0.1N NaOH | 7.9 | 15.4 |
| Ethylacetate | 2.2 | 3.2 |

Examples 2-4 demonstrate that a pre-formed therapeutic agent-substrate complex embedded into the hard, erodible, thermo-formable matrix is critical to generate a dosage form that is tamper-resistant and provides programmed extended release profiles. Examples 5 and 6 show that target dissolution profiles and tamper-resistance can be achieved whether the dosage form comprises tablets or multiparticulates, very surprising results not taught in the prior art. Examples 10 and 11 demonstrate that a variety of dissolution profiles with excellent tamper-resistance can be obtained consistently by a dry granulation process or a wet granulation process as long as the therapeutic agent-substrate complex is embedded within the thermo-formable matrix.

What is claimed is:

1. A process of preparing an erodible tamper-resistant dosage form, comprising the steps of:
   (1) blending at least one therapeutic agent and at least one substrate in a therapeutic agent-to-substrate ratio from 1:20 to 20:1 by weight;
   (2) reacting the at least one therapeutic agent and the at least one substrate to form a therapeutic agent-substrate complex using a twin-screw extruder;
   (3) forming a thermo-formable matrix blend with at least one thermoplastic polymer and at least one pharmaceutical additive;
   (4) mixing the therapeutic agent-substrate complex and the thermo-formable matrix blend in a ratio from 1:20 to 20:1 by weight;
   (5) granulating the therapeutic agent-substrate complex and the thermo-formable matrix blend to form the erodible tamper-resistant dosage form in which the therapeutic agent-substrate complex is embedded in the thermo-formable matrix;
   (6) shaping the tamper-resistant dosage form into one of an immediate release or modified release tablet form and an immediate release or modified release multiparticulate form; and
   (7) optionally, film-coating one of the tablet form and the multiparticulate form.

2. The process of claim 1, wherein the reacting step of (2) is carried out by a reactive extrusion process.

3. The process of claim 1, wherein the granulating step of (5) is carried out by a hot melt extrusion process.

4. The process of claim 1, wherein the granulating step of (5) is carried out by a wet granulation process.

5. The process of claim 1, wherein the granulating step of (5) is carried out by a dry granulation process.

* * * * *